United States Patent
McGinley et al.

(10) Patent No.: US 7,794,467 B2
(45) Date of Patent: Sep. 14, 2010

(54) ADJUSTABLE SURGICAL CUTTING SYSTEMS

(75) Inventors: Brian J. McGinley, Port Jefferson, NY (US); Daniel McCombs, Germantown, TN (US); Chester Paul Wheeler, Hernando, MI (US)

(73) Assignee: Smith & Nephew, Inc., Memphis, TN (US)

( * ) Notice: Subject to any disclaimer, the term of this patent is extended or adjusted under 35 U.S.C. 154(b) by 905 days.

(21) Appl. No.: 10/989,835

(22) Filed: Nov. 15, 2004

(65) Prior Publication Data

US 2005/0149041 A1     Jul. 7, 2005

Related U.S. Application Data

(60) Provisional application No. 60/520,097, filed on Nov. 14, 2003.

(51) Int. Cl.
*A61B 17/58* (2006.01)

(52) U.S. Cl. ........................................ 606/88

(58) Field of Classification Search .......... 606/86–89; 83/698.11, 698.51, 698.61, 699.31, 699.41, 83/699.51, 699.61
See application file for complete search history.

(56) References Cited

U.S. PATENT DOCUMENTS

| | | | |
|---|---|---|---|
| 100,602 A | 3/1870 | Coes | |
| 1,076,971 A | 10/1913 | Geiger | |
| 1,201,467 A | 10/1916 | Hoglund | |
| 2,092,869 A | 9/1937 | Baum | |
| 3,412,733 A | 11/1968 | Ross | |
| 3,457,922 A | 7/1969 | Ray | |
| 3,702,611 A | 11/1972 | Fishbein | |
| 4,305,394 A | 12/1981 | Bertuch, Jr. | |
| 4,323,080 A | 4/1982 | Melharty | |
| 4,421,112 A | 12/1983 | Mains et al. | |
| 4,456,010 A | 6/1984 | Reimels et al. | |
| 4,457,307 A | 7/1984 | Stillwell | |
| 4,483,554 A | 11/1984 | Ernst | |
| 4,524,766 A * | 6/1985 | Petersen | 606/88 |

(Continued)

FOREIGN PATENT DOCUMENTS

DE          042 25 112 C     12/1993

(Continued)

OTHER PUBLICATIONS

DePuy, a Johnson & Johnson Company, Brochure entitled 'S-ROM Modular Hip System Minimally Invasive Calcar Miller Surgical Technique,' 12 pages (2004).

(Continued)

*Primary Examiner*—Thomas C Barrett
*Assistant Examiner*—Nicholas Woodall
(74) *Attorney, Agent, or Firm*—Kilpatrick Stockton LLP

(57) ABSTRACT

Adjustable and modular systems, devices and methods for accurately cutting or resecting bones during surgery, particularly in preparation for installing joint implants during arthroplasties, including, but not limited to, preparation of femur or tibia during knee arthroplasties, such as total knee arthroplasty. The embodiments of the present invention provide solutions for adjusting a position of the cutting guides, or structures for guiding or directing the implements for resecting a patient's bone tissue, such as saws. The systems and devices comprise an adjustor for adjusting the cutting guide's position at the patient's bone in at least one degree of rotational freedom and in at least one degree of translational freedom.

17 Claims, 9 Drawing Sheets

U.S. PATENT DOCUMENTS

| | | |
|---|---|---|
| 4,534,364 A | 8/1985 | Lamoreux |
| 4,565,192 A | 1/1986 | Shapiro |
| 4,566,448 A | 1/1986 | Rohr, Jr. |
| 4,567,885 A | 2/1986 | Androphy |
| 4,567,886 A | 2/1986 | Petersen |
| 4,574,794 A | 3/1986 | Cooke et al. |
| 4,583,554 A | 4/1986 | Mittelman et al. |
| 4,671,275 A | 6/1987 | Deyerle |
| 4,703,751 A | 11/1987 | Pohl |
| 4,712,951 A | 12/1987 | Brown |
| 4,718,413 A | 1/1988 | Johnson |
| 4,722,056 A | 1/1988 | Roberts et al. |
| 4,738,256 A | 4/1988 | Freeman et al. |
| 4,759,350 A | 7/1988 | Dunn et al. |
| 4,768,504 A | 9/1988 | Ender |
| 4,777,942 A | 10/1988 | Frey et al. |
| 4,802,468 A | 2/1989 | Powlan |
| 4,803,976 A | 2/1989 | Frigg et al. |
| 4,809,689 A | 3/1989 | Anapliotis |
| 4,815,899 A | 3/1989 | Regan |
| 4,875,475 A | 10/1989 | Comte et al. |
| 4,892,093 A | 1/1990 | Zarnowski et al. |
| 4,913,163 A | 4/1990 | Roger et al. |
| 4,938,762 A | 7/1990 | Wehrli |
| 4,952,213 A | 8/1990 | Bowman et al. |
| 4,964,862 A | 10/1990 | Arms |
| 4,991,579 A | 2/1991 | Allen |
| 5,002,545 A | 3/1991 | Whiteside et al. |
| 5,002,578 A | 3/1991 | Luman |
| 5,016,639 A | 5/1991 | Allen |
| 5,037,423 A | 8/1991 | Kenna |
| 5,037,426 A | 8/1991 | Goble et al. |
| 5,049,149 A | 9/1991 | Schmidt |
| 5,053,039 A | 10/1991 | Hofmann et al. |
| 5,078,719 A | 1/1992 | Schreiber |
| 5,092,869 A | 3/1992 | Waldron |
| 5,094,241 A | 3/1992 | Allen |
| 5,097,839 A | 3/1992 | Allen |
| 5,098,426 A | 3/1992 | Sklar et al. |
| 5,116,338 A | 5/1992 | Poggie et al. |
| 5,119,817 A | 6/1992 | Allen |
| 5,122,144 A | 6/1992 | Bert et al. |
| 5,129,909 A | 7/1992 | Sutherland |
| 5,147,408 A | 9/1992 | Noble |
| 5,190,547 A | 3/1993 | Barber, Jr. et al. |
| 5,211,164 A | 5/1993 | Allen |
| 5,213,312 A | 5/1993 | MacDonald |
| 5,217,499 A | 6/1993 | Shelley |
| 5,230,338 A | 7/1993 | Allen et al. |
| 5,246,444 A | 9/1993 | Schreiber |
| 5,254,119 A | 10/1993 | Schreiber |
| 5,263,972 A | 11/1993 | Evans et al. |
| 5,289,826 A | 3/1994 | Kovacevic |
| 5,305,203 A | 4/1994 | Raab |
| 5,306,276 A * | 4/1994 | Johnson et al. ............ 606/86 R |
| 5,342,366 A | 8/1994 | Whiteside et al. |
| 5,342,368 A * | 8/1994 | Petersen ................... 606/88 |
| 5,360,016 A | 11/1994 | Kovacevic |
| 5,364,401 A | 11/1994 | Ferrante et al. |
| 5,364,402 A | 11/1994 | Mumme et al. |
| 5,365,996 A | 11/1994 | Crook |
| 5,375,588 A | 12/1994 | Yoon |
| 5,379,133 A | 1/1995 | Kirk |
| 5,383,454 A | 1/1995 | Bucholz |
| 5,387,218 A | 2/1995 | Meswania et al. |
| 5,389,101 A | 2/1995 | Heilbrun et al. |
| 5,395,376 A | 3/1995 | Caspari et al. |
| 5,397,329 A | 3/1995 | Allen |
| 5,403,320 A | 4/1995 | Luman |
| 5,423,828 A | 6/1995 | Benson |
| 5,425,355 A | 6/1995 | Kulick |
| 5,445,166 A | 8/1995 | Taylor |
| 5,445,642 A | 8/1995 | McNulty et al. |
| 5,449,360 A | 9/1995 | Schreiber |
| 5,452,407 A | 9/1995 | Crook |
| 5,462,548 A | 10/1995 | Pappas et al. |
| 5,462,549 A | 10/1995 | Glock |
| 5,468,244 A | 11/1995 | Attfield et al. |
| 5,470,354 A | 11/1995 | Hershberger et al. |
| 5,474,559 A | 12/1995 | Bertin et al. |
| 5,484,437 A | 1/1996 | Michelson |
| 5,486,178 A | 1/1996 | Hodge |
| 5,490,854 A | 2/1996 | Fisher et al. |
| 5,491,510 A | 2/1996 | Gove |
| 5,507,824 A | 4/1996 | Lennox |
| 5,514,139 A | 5/1996 | Goldstein et al. |
| 5,517,990 A | 5/1996 | Kalfas et al. |
| 5,527,316 A | 6/1996 | Williamson et al. |
| 5,540,691 A | 7/1996 | Elstrom et al. |
| 5,540,694 A | 7/1996 | DeCarlo, Jr. |
| 5,540,695 A | 7/1996 | Levy |
| 5,540,696 A | 7/1996 | Booth, Jr. et al. |
| 5,569,260 A | 10/1996 | Petersen |
| 5,597,379 A | 1/1997 | Haines et al. |
| 5,598,269 A | 1/1997 | Kitaevich et al. |
| 5,603,318 A | 2/1997 | Heilbrun et al. |
| 5,613,969 A | 3/1997 | Jenkins, Jr. |
| 5,643,268 A | 7/1997 | Vilsmeier et al. |
| 5,643,272 A | 7/1997 | Haines et al. |
| 5,658,290 A | 8/1997 | Lechot |
| 5,669,914 A | 9/1997 | Eckhoff |
| 5,676,668 A | 10/1997 | McCue et al. |
| 5,681,316 A * | 10/1997 | DeOrio et al. ................ 606/88 |
| 5,682,886 A | 11/1997 | Delp et al. |
| 5,683,397 A | 11/1997 | Vendrely et al. |
| 5,688,279 A | 11/1997 | McNulty et al. |
| 5,693,056 A | 12/1997 | Carls et al. |
| 5,695,501 A | 12/1997 | Carol et al. |
| 5,702,406 A | 12/1997 | Vilsmeier et al. |
| 5,704,941 A | 1/1998 | Jacober et al. |
| 5,707,370 A | 1/1998 | Berki et al. |
| 5,709,689 A | 1/1998 | Ferrante et al. |
| 5,715,836 A | 2/1998 | Kliegis et al. |
| 5,716,361 A | 2/1998 | Masini |
| 5,720,752 A | 2/1998 | Elliott et al. |
| 5,722,978 A | 3/1998 | Jenkins, Jr. |
| 5,733,292 A | 3/1998 | Gustilo et al. |
| 5,735,904 A | 4/1998 | Pappas |
| 5,743,915 A | 4/1998 | Bertin et al. |
| 5,748,767 A | 5/1998 | Raab |
| 5,755,725 A | 5/1998 | Druais |
| 5,755,803 A | 5/1998 | Haines et al. |
| 5,769,861 A | 6/1998 | Vilsmeier |
| 5,772,593 A | 6/1998 | Hakamata |
| 5,772,594 A | 6/1998 | Barrick |
| 5,776,064 A | 7/1998 | Kalfas et al. |
| 5,782,842 A | 7/1998 | Kloess et al. |
| 5,792,147 A | 8/1998 | Evans et al. |
| 5,797,924 A | 8/1998 | Schulte et al. |
| 5,799,055 A | 8/1998 | Peshkin et al. |
| 5,800,352 A | 9/1998 | Ferre et al. |
| 5,800,438 A | 9/1998 | Tuke et al. |
| 5,807,252 A | 9/1998 | Hassfeld et al. |
| 5,810,827 A | 9/1998 | Haines et al. |
| 5,810,841 A | 9/1998 | McNeirney et al. |
| 5,817,097 A | 10/1998 | Howard et al. |
| 5,830,214 A | 11/1998 | Flom et al. |
| 5,836,954 A | 11/1998 | Heilbrun et al. |
| 5,848,967 A | 12/1998 | Cosman |
| 5,850,836 A | 12/1998 | Steiger et al. |
| 5,860,981 A | 1/1999 | Bertin et al. |
| 5,865,809 A | 2/1999 | Moenning et al. |
| 5,871,018 A | 2/1999 | Delp et al. |
| 5,871,445 A | 2/1999 | Bucholz |

| Patent | Kind | Date | Inventor |
|---|---|---|---|
| 5,879,352 | A | 3/1999 | Filoso et al. |
| 5,879,354 | A | 3/1999 | Haines et al. |
| 5,880,976 | A | 3/1999 | DiGioia, III et al. |
| 5,885,296 | A | 3/1999 | Masini |
| 5,885,297 | A | 3/1999 | Matsen, III |
| 5,897,559 | A | 4/1999 | Masinie |
| 5,916,221 | A | 6/1999 | Hodorek et al. |
| 5,920,395 | A | 7/1999 | Schulz |
| 5,921,992 | A | 7/1999 | Costales et al. |
| 5,925,049 | A | 7/1999 | Gustilo et al. |
| 5,935,128 | A | 8/1999 | Carter et al. |
| 5,938,665 | A | 8/1999 | Martin |
| 5,944,722 | A | 8/1999 | Masini |
| 5,947,971 | A | 9/1999 | Kuslich et al. |
| 5,947,973 | A | 9/1999 | Masini |
| 5,951,561 | A | 9/1999 | Pepper et al. |
| 5,957,926 | A | 9/1999 | Masini |
| 5,961,523 | A | 10/1999 | Masini |
| 5,971,989 | A | 10/1999 | Masini |
| 5,980,526 | A | 11/1999 | Johnson et al. |
| 5,980,535 | A | 11/1999 | Barnett et al. |
| 5,999,837 | A | 12/1999 | Messner et al. |
| 6,001,106 | A | 12/1999 | Ryan et al. |
| 6,002,859 | A | 12/1999 | DiGioia, III et al. |
| 6,006,126 | A | 12/1999 | Cosman |
| 6,006,127 | A | 12/1999 | Van Der Brug et al. |
| 6,007,537 | A | 12/1999 | Burkinshaw et al. |
| 6,010,506 | A | 1/2000 | Gosney et al. |
| 6,011,987 | A | 1/2000 | Barnett |
| 6,016,606 | A | 1/2000 | Oliver et al. |
| 6,021,342 | A | 2/2000 | Brabrand |
| 6,021,343 | A | 2/2000 | Foley et al. |
| 6,022,377 | A | 2/2000 | Nuelle et al. |
| 6,026,315 | A | 2/2000 | Lenz et al. |
| 6,030,391 | A | 2/2000 | Brainard et al. |
| 6,033,410 | A | 3/2000 | McLean et al. |
| 6,041,249 | A | 3/2000 | Regn |
| 6,044,291 | A | 3/2000 | Rockseisen |
| 6,045,556 | A | 4/2000 | Cohen |
| 6,050,724 | A | 4/2000 | Schmitz et al. |
| 6,053,922 | A | 4/2000 | Krause et al. |
| 6,056,756 | A | 5/2000 | Eng et al. |
| 6,068,633 | A | 5/2000 | Masini |
| 6,069,932 | A | 5/2000 | Peshkin et al. |
| 6,073,044 | A | 6/2000 | Fitzpatrick et al. |
| 6,077,269 | A | 6/2000 | Masini |
| 6,081,336 | A | 6/2000 | Messner et al. |
| 6,083,163 | A | 7/2000 | Wegner et al. |
| 6,096,048 | A | 8/2000 | Howard et al. |
| 6,102,916 | A | 8/2000 | Masini |
| 6,132,433 | A | 10/2000 | Whelan |
| 6,143,390 | A | 11/2000 | Takamiya et al. |
| 6,144,875 | A | 11/2000 | Schweikard et al. |
| 6,146,390 | A | 11/2000 | Heilbrun et al. |
| 6,148,280 | A | 11/2000 | Kramer |
| 6,161,033 | A | 12/2000 | Kuhn |
| 6,162,190 | A | 12/2000 | Kramer |
| 6,165,181 | A | 12/2000 | Heilbrun et al. |
| 6,167,145 | A | 12/2000 | Foley et al. |
| 6,167,292 | A | 12/2000 | Badano et al. |
| 6,167,295 | A | 12/2000 | Cosman |
| 6,167,296 | A | 12/2000 | Shahidi |
| 6,168,627 | B1 | 1/2001 | Huebner |
| 6,174,335 | B1 | 1/2001 | Varieur |
| 6,185,315 | B1 | 2/2001 | Schmucker et al. |
| 6,187,010 | B1 | 2/2001 | Masini |
| 6,190,320 | B1 | 2/2001 | Lelong |
| 6,190,395 | B1 | 2/2001 | Williams |
| 6,195,168 | B1 | 2/2001 | De Lega et al. |
| 6,197,064 | B1 | 3/2001 | Haines et al. |
| 6,198,794 | B1 | 3/2001 | Peshkin et al. |
| 6,200,316 | B1 | 3/2001 | Zwirkoski et al. |
| 6,205,411 | B1 | 3/2001 | DiGioia, III et al. |
| 6,211,976 | B1 | 4/2001 | Popovich et al. |
| 6,214,011 | B1 | 4/2001 | Masini |
| 6,216,029 | B1 | 4/2001 | Paltieli |
| 6,223,067 | B1 | 4/2001 | Vilsmeier et al. |
| 6,226,548 | B1 | 5/2001 | Foley et al. |
| 6,228,090 | B1 | 5/2001 | Waddell |
| 6,228,092 | B1 | 5/2001 | Mikhail |
| 6,235,038 | B1 | 5/2001 | Hunter et al. |
| 6,236,875 | B1 | 5/2001 | Bucholz et al. |
| 6,241,735 | B1 | 6/2001 | Marmulla |
| 6,249,581 | B1 | 6/2001 | Kok |
| 6,258,095 | B1 | 7/2001 | Lombardo et al. |
| 6,258,096 | B1 | 7/2001 | Seki |
| 6,264,647 | B1 | 7/2001 | Lechot |
| 6,283,971 | B1 | 9/2001 | Temeles |
| 6,285,902 | B1 | 9/2001 | Kienzle, III et al. |
| 6,295,513 | B1 | 9/2001 | Thackston |
| 6,317,616 | B1 | 11/2001 | Glossop |
| 6,319,256 | B1 | 11/2001 | Spotorno |
| 6,332,891 | B1 | 12/2001 | Himes |
| 6,333,971 | B2 | 12/2001 | McCrory et al. |
| 6,344,853 | B1 | 2/2002 | Knight |
| 6,347,240 | B1 | 2/2002 | Foley et al. |
| 6,351,659 | B1 | 2/2002 | Vilsmeier |
| 6,351,661 | B1 | 2/2002 | Cosman |
| 6,377,839 | B1 | 4/2002 | Kalfas et al. |
| 6,383,188 | B2 | 5/2002 | Kuslich et al. |
| 6,385,475 | B1 | 5/2002 | Cinquin et al. |
| 6,405,072 | B1 | 6/2002 | Cosman |
| 6,413,261 | B1 | 7/2002 | Grundei |
| 6,434,507 | B1 | 8/2002 | Clayton et al. |
| 6,440,140 | B2 | 8/2002 | Bullivant et al. |
| 6,443,956 | B1 | 9/2002 | Ray |
| 6,451,059 | B1 | 9/2002 | Janas et al. |
| 6,458,135 | B1 | 10/2002 | Harwin et al. |
| 6,463,351 | B1 | 10/2002 | Clynch |
| 6,468,202 | B1 | 10/2002 | Irion et al. |
| 6,477,400 | B1 | 11/2002 | Barrick |
| 6,478,799 | B1 | 11/2002 | Williamson |
| 6,484,049 | B1 | 11/2002 | Seeley et al. |
| 6,490,467 | B1 | 12/2002 | Bucholz et al. |
| 6,491,429 | B1 | 12/2002 | Suhm |
| 6,491,702 | B2 | 12/2002 | Heilbrun et al. |
| 6,503,249 | B1 | 1/2003 | Krause |
| 6,503,254 | B2 | 1/2003 | Masini |
| 6,527,443 | B1 | 3/2003 | Vilsmeier et al. |
| 6,540,739 | B2 | 4/2003 | Lechot |
| 6,546,279 | B1 | 4/2003 | Bova et al. |
| 6,551,319 | B2 | 4/2003 | Lieberman |
| 6,551,324 | B2 | 4/2003 | Muller |
| 6,551,325 | B2 | 4/2003 | Neubauer et al. |
| 6,554,837 | B1 | 4/2003 | Hauri et al. |
| 6,558,391 | B2 | 5/2003 | Axelson, Jr. et al. |
| 6,558,421 | B1 | 5/2003 | Fell et al. |
| 6,567,687 | B2 | 5/2003 | Front et al. |
| 6,574,493 | B2 | 6/2003 | Rasche et al. |
| 6,595,997 | B2 | 7/2003 | Axelson, Jr. et al. |
| 6,602,259 | B1 | 8/2003 | Masini |
| 6,620,268 | B2 | 9/2003 | Cho et al. |
| 6,620,168 | B1 | 10/2003 | Lombardo et al. |
| 6,640,127 | B1 | 10/2003 | Kosaka et al. |
| 6,652,142 | B2 | 11/2003 | Launay et al. |
| 6,662,036 | B2 | 12/2003 | Cosman |
| 6,673,077 | B1 | 1/2004 | Katz |
| 6,675,040 | B1 | 1/2004 | Cosman |
| 6,685,711 | B2 * | 2/2004 | Axelson et al. ............ 606/88 |
| 6,690,964 | B2 | 2/2004 | Bieger et al. |
| 6,692,447 | B1 | 2/2004 | Picard |
| 6,695,848 | B2 | 2/2004 | Haines |
| 6,702,821 | B2 | 3/2004 | Bonutti |
| 6,711,431 | B2 | 3/2004 | Sarin et al. |
| 6,712,823 | B2 | 3/2004 | Grusin et al. |
| 6,712,824 | B2 | 3/2004 | Millard et al. |

| | | |
|---|---|---|
| 6,716,249 B2 | 4/2004 | Hyde |
| 6,718,194 B2 | 4/2004 | Kienzle |
| 6,725,080 B2 | 4/2004 | Melkent et al. |
| 6,725,082 B2 | 4/2004 | Sati et al. |
| 6,728,599 B2 | 4/2004 | Wang et al. |
| 6,772,026 B2 | 8/2004 | Bradbury et al. |
| 6,780,190 B2 | 8/2004 | Maroney |
| 6,785,593 B2 | 8/2004 | Wang |
| 6,799,088 B2 | 9/2004 | Wang |
| 6,814,490 B1 | 11/2004 | Suhm et al. |
| 6,827,723 B2 | 12/2004 | Carson |
| 6,836,703 B2 | 12/2004 | Wang |
| 6,871,117 B2 | 3/2005 | Wang |
| 6,882,982 B2 | 4/2005 | McMenimen |
| 6,892,112 B2 | 5/2005 | Wang |
| 6,905,514 B2 | 6/2005 | Carignan et al. |
| 6,923,817 B2 | 8/2005 | Carson |
| 6,947,786 B2 | 9/2005 | Simon et al. |
| 6,993,374 B2 | 1/2006 | Sasso |
| 7,001,346 B2 | 2/2006 | White |
| 7,035,702 B2 | 4/2006 | Jelonek et al. |
| 7,237,556 B2 | 7/2007 | Smothers |
| 7,241,298 B2 * | 7/2007 | Nemec et al. .............. 606/86 |
| 2001/0001120 A1 | 5/2001 | Masini |
| 2001/0014772 A1 | 8/2001 | Lampotang et al. |
| 2001/0016745 A1 | 8/2001 | Bullivant et al. |
| 2001/0034530 A1 | 10/2001 | Malackowski et al. |
| 2001/0036245 A1 | 11/2001 | Kienzle, III et al. |
| 2001/0039421 A1 | 11/2001 | Heilbrun et al. |
| 2002/0002330 A1 | 1/2002 | Vilsmeier |
| 2002/0002365 A1 | 1/2002 | Lechot |
| 2002/0007294 A1 | 1/2002 | Bradbury et al. |
| 2002/0011594 A1 | 1/2002 | DeSouza |
| 2002/0016540 A1 | 2/2002 | Mikus et al. |
| 2002/0018981 A1 | 2/2002 | Andersson et al. |
| 2002/0029041 A1 | 3/2002 | Hover et al. |
| 2002/0032451 A1 | 3/2002 | Tierney et al. |
| 2002/0038085 A1 | 3/2002 | Immerz |
| 2002/0052606 A1 | 5/2002 | Bonutti |
| 2002/0065461 A1 | 5/2002 | Cosman |
| 2002/0068942 A1 | 6/2002 | Neubauer et al. |
| 2002/0072748 A1 | 6/2002 | Robioneck |
| 2002/0072821 A1 | 6/2002 | Baker |
| 2002/0077533 A1 | 6/2002 | Bieger et al. |
| 2002/0077540 A1 | 6/2002 | Kienzle, III |
| 2002/0085681 A1 | 7/2002 | Jensen |
| 2002/0087101 A1 | 7/2002 | Barrick et al. |
| 2002/0095081 A1 | 7/2002 | Vilsmeier |
| 2002/0102214 A1 | 8/2002 | Briley-Saebo et al. |
| 2002/0107518 A1 | 8/2002 | Neubauer et al. |
| 2002/0115934 A1 | 8/2002 | Tuke |
| 2002/0133161 A1 | 9/2002 | Axelson et al. |
| 2002/0133175 A1 | 9/2002 | Carson |
| 2002/0147455 A1 | 10/2002 | Carson |
| 2002/0151894 A1 | 10/2002 | Melkent et al. |
| 2002/0151898 A1 | 10/2002 | Sohngen et al. |
| 2002/0156371 A1 | 10/2002 | Hedlund et al. |
| 2002/0156479 A1 | 10/2002 | Schulzki et al. |
| 2002/0188194 A1 | 12/2002 | Cosman |
| 2002/0193800 A1 | 12/2002 | Kienzle, III et al. |
| 2002/0198448 A1 | 12/2002 | Zuk et al. |
| 2002/0198451 A1 | 12/2002 | Carson |
| 2002/0198531 A1 * | 12/2002 | Millard et al. .............. 606/87 |
| 2003/0018338 A1 | 1/2003 | Axelson, Jr. et al. |
| 2003/0045883 A1 | 3/2003 | Chow et al. |
| 2003/0050643 A1 | 3/2003 | Taft |
| 2003/0065400 A1 | 4/2003 | Bradbury et al. |
| 2003/0069591 A1 | 4/2003 | Carson et al. |
| 2003/0073901 A1 | 4/2003 | Simon et al. |
| 2003/0153829 A1 | 8/2003 | Sarin et al. |
| 2003/0153859 A1 | 8/2003 | Hinshon |
| 2003/0153978 A1 | 8/2003 | Whiteside |
| 2003/0164172 A1 | 9/2003 | Chumas et al. |
| 2003/0181918 A1 | 9/2003 | Smothers et al. |
| 2003/0187351 A1 | 10/2003 | Franck et al. |
| 2003/0187452 A1 | 10/2003 | Smith et al. |
| 2003/0192557 A1 | 10/2003 | Krag et al. |
| 2003/0225329 A1 | 12/2003 | Rossner et al. |
| 2004/0019382 A1 | 1/2004 | Amirouche et al. |
| 2004/0030237 A1 | 2/2004 | Lee et al. |
| 2004/0030245 A1 | 2/2004 | Noble et al. |
| 2004/0039396 A1 * | 2/2004 | Couture et al. .............. 606/87 |
| 2004/0054489 A1 | 3/2004 | Moctezuma De La Barrera |
| 2004/0073279 A1 | 4/2004 | Malackowski et al. |
| 2004/0087852 A1 | 5/2004 | Chen et al. |
| 2004/0097952 A1 | 5/2004 | Sarin et al. |
| 2004/0152970 A1 | 8/2004 | Hunter et al. |
| 2004/0153081 A1 | 8/2004 | Tulkis |
| 2004/0153083 A1 * | 8/2004 | Nemec et al. .............. 606/86 |
| 2004/0167391 A1 | 8/2004 | Solar et al. |
| 2004/0171924 A1 | 9/2004 | Mire et al. |
| 2004/0243481 A1 | 12/2004 | Bradbury et al. |
| 2004/0254586 A1 | 12/2004 | Sarin |
| 2004/0260290 A1 | 12/2004 | Zander et al. |
| 2005/0021037 A1 | 1/2005 | McCombs et al. |
| 2005/0021043 A1 | 1/2005 | Jansen |
| 2005/0075632 A1 | 4/2005 | Russell et al. |
| 2005/0085715 A1 | 4/2005 | Dukesherer et al. |
| 2005/0085822 A1 | 4/2005 | Thornberry et al. |
| 2005/0101966 A1 | 5/2005 | Lavallee |
| 2005/0109855 A1 | 5/2005 | McCombs |
| 2005/0113658 A1 | 5/2005 | Jacobson et al. |
| 2005/0113659 A1 | 5/2005 | Pothier |
| 2005/0113846 A1 | 5/2005 | Carson |
| 2005/0119639 A1 | 6/2005 | McCombs |
| 2005/0119777 A1 | 6/2005 | Arbogast et al. |
| 2005/0124988 A1 | 6/2005 | Terrill-Grisoni et al. |
| 2005/0148843 A1 | 7/2005 | Roose |
| 2005/0149003 A1 | 7/2005 | Tierney et al. |
| 2005/0149041 A1 | 7/2005 | McGinley |
| 2005/0154331 A1 | 7/2005 | Christie et al. |
| 2005/0159759 A1 | 7/2005 | Harbaugh et al. |
| 2005/0177172 A1 | 8/2005 | Acker |
| 2005/0197569 A1 | 9/2005 | McCombs |
| 2005/0203384 A1 | 9/2005 | Sati et al. |
| 2005/0209726 A1 | 9/2005 | Voit et al. |
| 2005/0216305 A1 | 9/2005 | Funderud |
| 2005/0228266 A1 | 10/2005 | McCombs |
| 2005/0228404 A1 | 10/2005 | Vandevelde |
| 2005/0234332 A1 | 10/2005 | Murphy |
| 2005/0234465 A1 | 10/2005 | McCombs |
| 2005/0234466 A1 | 10/2005 | Stallings |
| 2005/0234468 A1 | 10/2005 | Carson |
| 2005/0245808 A1 | 11/2005 | Carson |
| 2005/0279368 A1 | 12/2005 | McCombs |
| 2005/0288676 A1 | 12/2005 | Schnieders |
| 2006/0015120 A1 | 1/2006 | Richard et al. |
| 2006/0161051 A1 | 7/2006 | Terrill-Grisoni et al. |
| 2006/0190011 A1 | 8/2006 | Ries |
| 2006/0200025 A1 | 9/2006 | Elliott |
| 2006/0229626 A1 | 10/2006 | McLean |
| 2007/0118055 A1 | 5/2007 | McCombs |
| 2007/0123912 A1 | 5/2007 | Carson |
| 2007/0169782 A1 | 7/2007 | Castleman et al. |

FOREIGN PATENT DOCUMENTS

| | | |
|---|---|---|
| DE | 296 00 990 | 1/1996 |
| DE | 196 29 011 A1 | 1/1998 |
| DE | 197 09 960 A | 9/1998 |
| DE | 299 06 438 U1 | 9/1999 |
| DE | 296 23 941 U1 | 11/2000 |
| DE | 200 21 494 | 3/2001 |
| DE | 201 03 416 U1 | 7/2001 |
| DE | 100 12 042 | 8/2001 |
| DE | 100 31 887 A1 | 1/2002 |

| | | |
|---|---|---|
| DE | 102 07 035 | 2/2002 |
| DE | 100 45 381 A1 | 4/2002 |
| DE | 202 13 243 | 10/2002 |
| DE | 203 09 399 | 8/2003 |
| EP | 0 327 509 A1 | 8/1989 |
| EP | 0 327 509 B1 | 8/1989 |
| EP | 0 337 901 A1 | 10/1989 |
| EP | 0 340 176 A2 | 11/1989 |
| EP | 0 216 794 B1 | 12/1989 |
| EP | 0 366 488 B1 | 5/1990 |
| EP | 0 376 657 B1 | 7/1990 |
| EP | 0 380 451 A2 | 8/1990 |
| EP | 0 415 837 A2 | 3/1991 |
| EP | 0 466 659 A2 | 1/1992 |
| EP | 0 359 097 | 8/1992 |
| EP | 0 538 152 A1 | 4/1993 |
| EP | 0 538 153 B1 | 4/1993 |
| EP | 0 555 003 B1 | 8/1993 |
| EP | 0 428 303 | 7/1995 |
| EP | 0 676 178 A | 10/1995 |
| EP | 0 720 834 A2 | 7/1996 |
| EP | 0 619 097 | 6/1999 |
| EP | 1 149 562 A2 | 10/2001 |
| EP | 1 033 108 | 2/2002 |
| EP | 1 190 676 B1 | 3/2002 |
| EP | 1 226 788 | 7/2002 |
| EP | 1 226 788 A1 | 7/2002 |
| EP | 0 782 842 | 9/2002 |
| EP | 1 236 450 A1 | 9/2002 |
| EP | 1 249 207 | 10/2002 |
| EP | 1 348 384 | 10/2003 |
| EP | 1 384 456 A2 | 1/2004 |
| EP | 1 405 603 A2 | 4/2004 |
| EP | 1 406 203 | 4/2004 |
| EP | 1 435 223 A1 | 7/2004 |
| EP | 1 442 715 | 8/2004 |
| EP | 1 459 686 A2 | 9/2004 |
| EP | 1 532 946 A2 | 5/2005 |
| EP | 1 563 795 | 8/2005 |
| FR | 2 828 397 | 2/2003 |
| GB | 2 224 937 | 5/1990 |
| GB | 2 397 769 A | 8/2004 |
| JP | 2002-304439 | 10/2002 |
| WO | WO 86/05384 | 9/1986 |
| WO | WO 89/09570 | 10/1989 |
| WO | WO 94/17733 | 8/1994 |
| WO | WO 95/15714 | 6/1995 |
| WO | WO 96/35387 | 11/1996 |
| WO | WO 97/16129 | 5/1997 |
| WO | WO 97/23172 | 7/1997 |
| WO | WO 97/29683 | 8/1997 |
| WO | WO 98/29032 | 7/1998 |
| WO | WO 98/46169 | 10/1998 |
| WO | WO 99/15097 | 4/1999 |
| WO | WO 99/27860 | 6/1999 |
| WO | WO 99/60939 | 12/1999 |
| WO | WO 99/65380 | 12/1999 |
| WO | WO 00/00093 | 1/2000 |
| WO | WO 00/21442 | 4/2000 |
| WO | WO 00/47103 | 8/2000 |
| WO | WO 00/64367 | 11/2000 |
| WO | WO 01/01845 A2 | 1/2001 |
| WO | WO 01/19271 A2 | 3/2001 |
| WO | WO 01/34050 A2 | 5/2001 |
| WO | WO 01/34050 A3 | 5/2001 |
| WO | WO 01/64124 A1 | 9/2001 |
| WO | WO 01/67979 A1 | 9/2001 |
| WO | WO 01/91647 A1 | 12/2001 |
| WO | WO 01/93770 A1 | 12/2001 |
| WO | WO 02/24096 A1 | 3/2002 |
| WO | WO 02/041794 A1 | 5/2002 |
| WO | WO 02/063236 A1 | 8/2002 |
| WO | WO 02/063236 A3 | 8/2002 |
| WO | WO 02/064042 | 8/2002 |
| WO | WO 02/067783 | 9/2002 |
| WO | WO 02/067784 | 9/2002 |
| WO | WO 02/067800 | 9/2002 |
| WO | WO 02/080824 A1 | 10/2002 |
| WO | WO 03/006107 | 1/2003 |
| WO | WO 03/015642 | 2/2003 |
| WO | WO 03/030787 | 4/2003 |
| WO | WO 03/034213 A2 | 4/2003 |
| WO | WO 03/034933 A1 | 5/2003 |
| WO | WO 03/037192 A1 | 5/2003 |
| WO | WO 03/039377 | 5/2003 |
| WO | WO 03/041566 A2 | 5/2003 |
| WO | WO 03/065931 | 8/2003 |
| WO | WO 03/065949 A2 | 8/2003 |
| WO | WO 03/068090 A1 | 8/2003 |
| WO | WO 03/071969 A1 | 9/2003 |
| WO | WO 03/075740 A2 | 9/2003 |
| WO | WO 03/079940 | 10/2003 |
| WO | WO 03/096870 A2 | 11/2003 |
| WO | WO 2004/001569 A2 | 12/2003 |
| WO | WO 2004/017842 A2 | 3/2004 |
| WO | WO 2004/019792 | 3/2004 |
| WO | WO 2004/029908 A1 | 4/2004 |
| WO | WO 2004/030556 A2 | 4/2004 |
| WO | WO 2004/030559 A1 | 4/2004 |
| WO | WO 2004/046754 A2 | 6/2004 |
| WO | WO 2004/069036 | 8/2004 |
| WO | WO 2004/070580 | 8/2004 |
| WO | WO 2004/008740 A1 | 10/2004 |
| WO | WO 2004/084740 | 10/2004 |
| WO | WO 2005/009303 A1 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO2005/048851 A1 | 6/2005 |
| WO | WO2005/053559 A1 | 6/2005 |
| WO | WO 2005/057439 | 6/2005 |
| WO | WO2005/070312 A1 | 8/2005 |
| WO | WO 2005/070319 A1 | 8/2005 |
| WO | WO 2005/072629 A1 | 8/2005 |
| WO | WO 2005/096982 | 10/2005 |
| WO | WO 2005/104977 | 11/2005 |
| WO | WO 2005/104978 | 11/2005 |
| WO | WO 2006/044367 A1 | 4/2006 |
| WO | WO 2006/060631 A1 | 6/2006 |
| WO | WO 2006/078236 A1 | 7/2006 |
| WO | WO 2008/021494 | 2/2008 |

OTHER PUBLICATIONS

Hafez, et al., 'Computer-assisted Total Knee Arthroplasty Using Patient-specific Templating,' *Clinical Orthopaedics and Related Research*, No. 444, pp. 184-192 (2006).
National Institute of Arthritis and Musculoskeletal and Skin Diseases (NIAMS), "Questions & Answers about . . . Knee Problems", 36 pp. (May 2001).
"implant" Merriam-Webster Online Dictionary [online], Retrieved from the Internet <URL: www.m-w.com.
Smith & Nephew Total Hip Replacement Surgery, HipReplacementInfo.com, 3 pages, Nov. 8, 2005 http://www/hipreplacementinfo.com/hip-total-replacement.htm.
Smith & Nephew Brochure, Design Features, "Opera" pp. 4-15 (1999).
Corinth Surgeon Performs Revolutionary Hip Replacement, Mississippi Medical News, pp. 1-2 (Nov. 17, 2005) http://host1.bondware.com/~mississippi/news.php?viewStory=347.
Dario, et al., 'Smart Surgical Tools and Augmenting Devices,' IEEE Trans. Rob. Autom., 19(5):782-792 (2003).
Fernandez-Lozano, et al., 'Human-machine interface evaluation in a computer assisted surgical system,' Proc. IEEE Int. Conf. Rob. Autom., 2004:231-236 (2004).

Martelli, et al., 'Criteria of interface evaluation for computer assisted surgery systems,' Int. J. Med. Informatics, 72:35-45 (2003).
Visarius, et al., 'Man-machine interfaces in computer assisted surgery,' Computer Aided Surgery, pp. 102-107 (2004).
AO Development Institute "MEPUC Motorized Exact Positioning Unit for C-arm," one page (Jul. 7, 2003) http://www.ao-asif.ch/development/adi/examples/mepuc.shtml.
AO Development Institute "MEPUC Motorized Exact Positioning Unit . . . " one page (Mar. 26, 2003) http://www/ao-asif.ch/development/adi/examples/mepuc.shtml.
Barnes, et al., "Unicompartmental Knee Arthroplasty," Bombay Hospital Journal, Issue Special, pp. 1-5, www.bhj.org/journal/1996/3803_july/special_486.htm.
Bonecraft Carnegie Mellon Computer-Aided Bone Deformity Correction Brochure, pp. 1-5 (undated).
Bonutti, "Total Joint Replacement Surgery in the 21$^{st}$ Century—New 'Limited-Incision' Total Knee Replacement Offers Important Advantages," 01 page (undated).
Bonutti, et al., "Minimal Incision Total Knee Arthroplasty Using the Suspended Leg Technique," Orthopedics, (published Sep. 2003), 6 pages http://www.orthobluejournal.com/0903/9tips.asp.
BrainLAB Brochure entitled "Ortho . . . Your Partner for the Future" pp. 1-28 (2002).
Croitoru, et al., "Fixation-Based Surgery: A New Technique for Distal Radius Osteotomy," Clinical Paper, Computer Aided Surgery 2001, 160-169, vol. 6 (2001).
Delp, et al., "Computer-Assisted Knee Replacement," Clinical Orthopaedics and Related Research, 354:49-56 (1998).
Deluzio, et al., "Static alignment and the adduction moment in unicompartmental arthroplasty patients," Presented at NACOB 98: North American Congress on Biomechanics, University of Waterloo, Ontario, Canada, Aug. 14-18, 1998.
DiGioia, et al., "Computer Assisted Orthopedic Surgery," Clinical Orthopaedics and Related Research, Sep. 1998, vol. 354, pp. 8-16.
Ellis, et al., "A Surgical Planning and Guidance System for High Tibial Osteotomy," Journal of Computer-Assisted Surgery, 4(5):264-274 (1999).
Foley, et al., "Percutaneous pedicle screw fixation of the lumbar spine," Neurosurg. Focus, vol. 10(4), pp. 1-8 (2001).
Glossop, http:/www/traxta.com/papers/cua/mode1.html, 8 pages (Feb. 6, 2002).
iON™ Smith & Nephew Orthopaedics Brochure entitled "You'll Never Look At Your Patients the Same Way Again." 10 pages (Jan. 2001).
Iyun, et al., "Planning and Performing the Ilizarov Method with the Taylor Spatial Frame," Abstract, at 2$^{nd}$ Annual Meeting of International Society for Computer Assisted Orthopaedic Surgery, Jun. 21, 2002, pp. 145-147.
Kanade, et al., "Image-Based Computer Assisted Orthopedic Surgery System," Bonecraft, Inc., 12 pages, Apr. 30, 2001.
Kiefer, et al., "Computer Aided Knee Arthroplasty Versus Conventional Technique—First Results," First Annual Meeting of the International Society for Computer Assisted Orthopedic Surgery, Davos, Switzerland, Feb. 8-10, 2001.
Kunz, et al., "Development and Verification of a Non-CT Based Total Knee Arthroplasty System for the LCS Prosthesis," First Annual Meeting of the International Society for Computer Assisted Orthopedic Surgery, Davos, Switzerland, Feb. 8-10, 2001.
Medtronic Surgical Navigation Technologies "Overview Image-Guided Surgery an Advanced Solution to Traditional Surgery," two pages (undated).
Medtronic Surgical Navigation Technologies SNT VERTEK photograph, one page (undated).
Medtronic Surgical Navigation Technologies System Components photograph Vertek Platform, one page (undated).
Munoz, et al., "Computer Assisted Planning of Hig Tibial Osteotomy for the Treatment of Knee Osteoarthritis," http://www.utc.fr/esb/esb09/abs_htm/570.html (Feb. 21, 2002) (three pages).
Patent Abstracts of Japan, vol. 2002, No. 05, May 3, 2002 & JP 2002 017740A (Ochi Takahiro; Yonenobu Sakuo: MMT:KK) Jan. 22, 2002 Abstract.
Picard, et al., "Kneenay.TKR: Concept and Clinical Application," Computer Assisted Orthopedic Surgery USA 2000 Meeting, Pittsburgh, PA., Jun. 15-17, 2000.
Saragaglia, et al., "Computer Assisted Total Knee Arthroplasty: Comparison with a Conventional Procedure. Results of a 50 Cases Prospective Randomized Study," First Annual Meeting of the International Society for Computer Assisted Orthopedic Surgery, Davos, Switzerland, Feb. 8-10, 2001.
Simon, et al., "The Fundamentals of Virtual Fluoroscopy," Medtronic Surgical Navigation Technologies, Medtronic, pp. 57-66, Computer Assisted Orthopedic Surgery USA 2000 Meeting, Pittsburgh, PA, Jun. 15-17, 2000.
Smith & Nephew—Orthopaedics—CAS—Knees Computer Assisted Total Knee Replacement Surgery, 02 pages (Oct. 13, 2004) http://ortho.smith-nephew.com/us/Standard.asp?NodeId=3396.
Smith & Nephew—Orthopaedics—TriGen Flexible Reamer System http://www.smithnephew.com/US/Standard.asp?NodeID=2998, 02 pages (Jan. 21, 2003).
Smith & Nephew—Orthopaedics—TriGen Reducer http://www.smithnephew.com/US/Standard.asp?NodeID=2996, one page (Jan. 21, 2003).
Smith & Nephew Brochure entitled "Surgical Technique Mini Incision Hip Posterior Approach," 20 pages (Mar. 2003).
Smith & Nephew First Choice in Orthopaedics Brochure Entitled "Achieve Computer Assisted Surgery Trauma Applications The Orbiter Base Station & Satellite Surgical Platform," 18 pages (undated).
Smith & Nephew Genesis II "Total Knee System Primary Surgical Technique," Brochure, pp. 1-36 (Mar. 2001).
Smith & Nephew Orthopaedic product bulletin, 01 page.
Smith & Nephew Richards Genesis® "Total Knee System Primary Surgical Technique Anterior Referencing Instrumentation," pp. 59 (Dec. 1993).
Smith & Nephew Richards Genesis® Total Knee System, "Revision Posterior Referencing Instrumentaion Surgical Technique," Brochure, pp. 1-51 (Dec. 1993).
Stryker Navigation System brochure entitled " . . . best alignment for gap kinematics," 6 pages (2001).
Sugano, et al., "Medical Robotics and Computer-Assisted Surgery in the Surgical Treatment of Patients and Rheumatic Diseases," Cutting Edge Reports, http://www/rheuma2lst.com/archives/cutting_edge_Robotics_Japan.html (Apr. 27, 2000).
Suhm, et al., "Adapting the C-Arm Fluoroscope for Image Guided Orthopaedic Surgery," CAOS, pp. 212-214 (2002).
Tenbusch, et al., "First Results Using the Robodoc® System for Total Knee Replacement," First Annual Meeting of the International Society for Computer Assisted Orthopedic Surgrey, Davos, Switzerland, Feb. 8-10, 2001.
Tricon Total Knee System, "Tricon-M® with Pro-FIT™ Surgical Procedures," Richards Brochure, pp. 1-29 (undated).
Valstar, et al., "Towards computer-assisted surgery in should joint replacement," ISPRS Journal of Photogrammetry & Remote Sensing, 56:326-337 (2002).

* cited by examiner

ADJUSTABLE SURGICAL CUTTING SYSTEMS

CROSS-REFERENCE TO RELATED APPLICATION

This application claims the benefit of U.S. Provisional Patent Application Ser. No. 60/520,097 entitled "Minimally Invasive Surgery Cutting Block" filed on Nov. 14, 2003, the entire content of which is incorporated herein.

FIELD OF THE INVENTION

The present invention relates generally to systems, devices and methods for preparing bones for installing joint implants during joint replacement surgery. More specifically, the present invention relates to adjustable systems for cutting bones during joint replacement surgery, particularly to adjustable surgical cutting blocks for resecting femoral or tibial bones, or both, during total knee replacement surgery, or total knee arthroplasty.

BACKGROUND

Joint implants, also referred to as joint prostheses, joint prosthetic implants, joint replacements, or prosthetic joints, are long-term surgically implantable devices that are used to partially or totally replace within the musculoskeletal system of a human or an animal diseased or damaged joints, such as, but not limited to, a knee, a hip, a shoulder, an ankle, or an elbow joint. Since their first introduction into clinical practice in the 1960s, joint implants have improved the quality of life of many patients.

Knee arthroplasty is a procedure for replacing components of a knee joint damaged by trauma or disease. During this procedure, a surgeon removes a portion of one or more knee bones forming the knee joint and installs prosthetic components to form the new joint surfaces. In the United States alone, surgeons perform approximately 250,000 total knee arthroplasties (TKAs), or total replacements of a knee joint, annually. Thus, it is highly desirable to improve this popular technique to ensure better restoration of knee joint function and shortening the patient's recovery time.

The human knee joint includes essentially includes four bones. The lower extremity of the femur, or distal femur, attaches by ligaments and a capsule to the proximal tibia. The distal femur contains two rounded oblong eminences, the condyles, separated by an intercondylar notch. The tibia and the femur do not interlock but meet at their ends. The femoral condyles rest on the condyles of the proximal tibia. The fibula, the smaller shin bone, attaches just below the tibia and is parallel to it. The patella, or knee cap, is at the front of the knee, protecting the joint and providing extra leverage. A patellar surface is a smooth shallow articular depression between the femoral condyles at the front. Cartilage lines the surfaces of the knee bones, cushions them, and minimizes friction. Two C-shaped menisci, or meniscal cartilage, lie between the femur and the tibia, serve as pockets for the condyles, and stabilize the knee. Several ligaments connect the knee bones and cover and stabilize the joint. The knee ligaments include the patellar ligament, the medial and lateral collateral ligaments, and the anterior (ACL) and posterior (PCS) cruciate ligaments. Ligaments and cartilage provide the strength needed to support the weight of the upper body and to absorb the impact of exercise and activity. A bursa, or sack, surrounds the knee joints and contains lubricating fluid.

A healthy knee allows the leg to move freely within its range of motion while supporting the upper body and absorbing the impact of its weight during motion. The knee has generally six degrees of motion during dynamic activities: three rotations (flexion/extension angulations, axial rotation along the long axis of a large tubular bone, also referred to as interior/exterior rotation, and varus/valgus angulations); and three translations (anterior/posterior, medial/lateral, and superior/inferior).

A total knee arthroplasty, or TKA, replaces both the femoral component and the tibial component of the damaged or affected by disease knee with artificial components made of synthetic materials, including, but not limited to, metals, ceramics, plastics, or combinations of them. These prosthetic knee components are attached to the bones, and existing ligaments and muscles are used to stabilize the artificial knee. During TKA, after preparing and anesthetizing the patient, the surgeon makes a long incision along the front of the knee and positions the patella to expose the joint. After exposing the ends of the bones, the surgeon removes the damaged tissue and cuts, or resects, the portions of the tibial and femoral bones to prepare the surfaces for installation of the prosthetic components. After preparation of the bones, the knee is tested with the trial components. Ligament balancing, including any necessary surgical release or contraction of the knee ligaments, is performed to ensure proper selection of the prosthetic components and post-operative functioning of the knee. Both anatomic (bone-derived landmarks) and dynamic or kinematic (ligament and bone interactions during the knee movement) data are usually considered when determining surgical cuts and positioning of the prosthetic components. After ligament balancing and proper selection of the components, the surgeon installs and secures the tibial and femoral components. The patella is resurfaced before or after installation of the tibial and femoral component, and a small plastic piece is often placed on the rear side, where it will cover the new joint. After installation of the knee prosthesis, the knee is closed according to conventional surgical procedures. Post-operative rehabilitation starts shortly after the surgery to restore the knee's function.

Improper positioning and misalignment of the prosthetic knee components commonly cause prosthetic knees to fail, leading to revision surgeries. This failure increases the risks associated with knee replacement, especially because many patients requiring prosthetic knee components are elderly and highly prone to the medical complications resulting from multiple surgeries. Also, having to perform revision surgeries greatly increases the medical costs associated with the restoration of the knee function. In order to prevent premature, excessive, or uneven wear of the artificial knee, the surgeon must implant the prosthetic device so that its multiple components articulate at exact angles. Thus, correctly preparing the bone for installation of the prosthetic components by precisely determining and accurately performing all the required bone cuts is vital to the success of TKR.

The surgeons generally rely heavily on their experience to determine where the bone should be cut. They also use various measuring and indexing devices to determine the location of the cut, and various guiding devices, such as, but not limited to, guides, jigs, blocks and templates, to guide the saw blades to accurately resect the bones. After determining the desired position of the cut, the surgeon usually attaches the guiding device to the bone using appropriate fastening mechanisms, including, but not limited to, pins and screws. Attachment to structures already stabilized relative to the bone, such as intramedullary rods, can also be employed.

After stabilizing the guiding device at the bone, the surgeon uses the guiding component of the device to direct the saw blade in the plane of the cut.

To properly prepare femoral surfaces to accept the femoral component of the prosthetic knee, the surgeon needs to accurately determine the position of and perform multiple cuts, including, but not limited to, a transversely directed distal femoral cut, an axially directed anterior femoral cut, an axially directed posterior femoral cut, anterior and posterior chamfer femoral cuts, a trochlear recess cut, or any combination or variation of those. Preparation of the tibia for installation of the tibial component may also involve multiple cuts. Sequentially attaching to the bone and properly positioning a series of cutting guides, each adapted for a specific task, lengthens and complicates the TKR procedure. This problem is particularly pressing in the context of the so-called "minimally invasive surgery" (MIS) techniques.

The term "minimally invasive surgery" generally refers to the surgical techniques that minimize the size of the surgical incision and trauma to tissues. Minimally invasive surgery is generally less intrusive than conventional surgery, thereby shortening both surgical time and recovery time. Minimally invasive TKA techniques are advantageous over conventional TKA techniques by providing, for example, a smaller incision, less soft-tissue exposure, improved collateral ligament balancing, and minimal trauma to the extensor mechanism (see, for example, Bonutti, P.M., et al., Minimal Incision Total Knee Arthroplasty Using the Suspended Leg Technique, *Orthopedics*, September 2003). To achieve the above goals of MIS, it is necessary to modify the traditional implants and instruments that require long surgical cuts and extensive exposure of the internal knee structures. To make the knee implants and knee arthroplasty instruments, structures, and devices particularly suitable for minimally invasive surgical procedures, it is desirable to decrease their size and the number of components. Cutting systems and devices for MIS are desired that can be installed and adjusted with minimal trauma to the knee's tissues and allow the surgeon to perform the cuts quickly and efficiently without compromising the accuracy of the resection. Also desired are cutting systems and devices that minimize the number of the surgical steps required to accurately cut the bones in preparation for installation of the prosthetic knees.

Another recent development in TKA is computer-assisted surgical systems that use various imaging and tracking devices and combine the image information with computer algorithms to track the position of the patient's leg, the implant, and the surgical instruments and make highly individualized recommendations on the most optimal surgical cuts and prosthetic component selection and positioning. Several providers have developed and marketed imaging systems based on CT scans and/or MRI data or on digitized points on the anatomy. Other systems align preoperative CT scans, MRIs, or other images with intraoperative patient positions. A preoperative planning system allows the surgeon to select reference points and to determine the final implant position. Intraoperatively, the system calibrates the patient position to that preoperative plan, such as using a "point cloud" technique, and can use a robot to make femoral and tibial preparations. Other systems use position and/or orientation tracking sensors, such as infrared sensors acting stereoscopically or otherwise, to track positions of body parts, surgery-related items such as implements, instrumentation, trial prosthetics, prosthetic components, and virtual constructs or references such as rotational axes which have been calculated and stored based on designation of bone landmarks. Processing capability such as any desired form of computer functionality, whether standalone, networked, or otherwise, takes into account the position and orientation information as to various items in the position sensing field (which may correspond generally or specifically to all or portions or more than all of the surgical field) based on sensed position and orientation of their associated fiducials or based on stored position and/or orientation information. The processing functionality correlates this position and orientation information for each object with stored information regarding the items, such as a computerized fluoroscopic imaged file of a femur or tibia, a wire frame data file for rendering a representation of an instrumentation component, trial prosthesis or actual prosthesis, or a computer generated file relating to a rotational axis or other virtual construct or reference. The processing functionality then displays position and orientation of these objects on a screen or monitor, or otherwise. The surgeon may navigate tools, instrumentation, trial prostheses, actual prostheses and other items relative to bones and other body parts to perform TKAs more accurately, efficiently, and with better alignment and stability.

With the introduction of the computer-assisted surgical systems, adjustable systems for cutting the bone during TKR became particularly desired. Although some providers developed adjustable cutting blocks, their adjustment capabilities were generally limited to setting a parameter, such as the varus/valgus angle, prior to installation of the cutting block The cutting systems capable of being adjusted continuously during surgery were not desirable, because the surgeon was not able to follow the position of the installed cutting block after adjustment. Once the computer-aided systems and processes became available that can provide useful data throughout TKR surgery on predicted or actual position and orientation of body parts, surgically related items, implants, and virtual constructs for use in navigation, assessment, and otherwise performing surgery or other operations, cutting systems became particularly desirable whose position can be continually adjusted after taking into account the feedback from the computer functionality. Additionally, the known adjustable cutting systems are not suitable for minimally invasive surgery, because they are generally too large to be placed in a small incision, too cumbersome to use, and require additional mechanical referencing devices for proper positioning and adjustment.

Thus, multifunctional systems for guiding bone cuts during TKR are needed that are particularly well adapted for use in minimally invasive surgery, computer-assisted surgery, or both. To this end, cutting systems or devices are needed that are smaller than conventional cutting systems and devices, and allow the surgeon to minimize the size of the surgical incision and tissue damage, thereby reducing the surgical repairs and shortening the recovery time. Cutting systems and devices are needed that minimize damage the bone during installation. Cutting systems and devices are needed that can be positioned and installed at the bone without the encumbrances of mechanical referencing devices. Further, cutting systems and devices are needed whose position can be precisely controlled before and after installation so that it is possible to place them accurately in the desired location suggested by the navigation system. Also, there is an unrealized need in cutting systems and devices with multiple adjustment parameters. Particularly, systems and devices are desired that are adjustable in multiple angles of rotation and multiple translations, but miniature enough to be useful for minimal invasive surgery, thereby reducing patient visit time and costs, and potential of infection. In general, surgical cutting guides are needed for use in TKA that are easy to use and manufacture, minimize tissue damage, simplify surgical procedures, are robust, can withstand multiple surgeries and required sterilization treatments, are versatile, allow for faster healing with fewer complications, require less post-surgical immobilization, are simple to use so as to require less operator training, and also less costly to produce and operate.

SUMMARY

The aspects and embodiments of the present invention provide novel systems, devices and methods for accurately cutting or resecting bones during surgery. In a preferred embodiment, the systems, devices, and methods are for resecting bones in preparation for installing joint implants during arthroplasties, including, but not limited to, preparation of the femur or tibia during knee arthroplasties, such as total knee arthroplasty. Certain aspects and embodiments of the present invention provide novel solutions for adjusting a position of the cutting guides, or structures for guiding or directing the implements for resecting a patient's bone tissue, such as saws.

The systems and devices according to aspects and embodiments of the present invention are adjustable and modular. The systems and devices according to the aspects and embodiments of the present invention comprise an adjustor module, or adjustor, for adjusting the cutting guide's position at the patient's bone in at least one degree of rotational freedom and in at least one degree of translational freedom and comprising structures for adjusting the cutting guide's position in at least one degree of translational freedom, at least one degree of rotational freedom, or both. During adjustment, the adjustor is attached, affixed, adjoined, fastened, connected to, or otherwise stabilized in space relative to the patient, and operably connected to the cutting guide that is free to move relative to the patient. Manipulating the adjustor moves the cutting guide, thereby adjusting its position relative to the bone.

Compared to conventional adjustable cutting guides and systems, the systems according to aspects and embodiments of the present invention advantageously allow a user to adjust the position of cutting guides relative to a patient throughout the surgical procedure. Many conventional systems fail to provide for adjustment of position of the cutting guides after their initial installation. They have to be adjusted prior to their installation in the surgical field, forcing the user to rely on the preliminary estimates of the cutting guide's position, not necessarily accurate. In contrast, the systems according to the aspects and embodiments of the present invention are initially generally located and installed relative to the patient based on any suitable technique available to the user, followed by precisely adjusting the position of the cutting guide by manipulating the adjustor module. Upon adjustment, the cutting guide is affixed or otherwise stabilized relative to the bone and is used to direct the cutting implement in bone resection.

The modular structure of the systems and devices according to the aspects and embodiments of the present invention increases their versatility compared to conventional devices. In one aspect, the modular structure improves the versatility by allowing modification of the systems' components quickly and easily. For example, combining the adjustor modules and the cutting guides in various arrangements is possible. Further improving the system's versatility, the adjustor modules can be stabilized with respect to the patient either by directly attaching them to the bone, or indirectly, by attaching the adjustor to structures affixed or stabilized with respect to the patient. For example, an adjustor can be attached to pre-installed intramedullary rods or anchor posts, thereby providing and additional opportunity for positioning relative to the patient.

The adjustability of the systems and devices according to aspects and embodiments of the present invention allows their installation in a variety of patients and their use for preparation of bones differing in size and shape in different surgical applications. By incorporating multiple adjustment capabilities, the dimensions and position of the systems and devices according to aspects and embodiments of the present invention are easier and more accurate to adjust than those of conventional devices.

Although suitable for a variety of applications, the modular adjustable systems devices according to aspects and embodiments of the present invention are particularly advantageous for minimally invasive surgeries, such as minimally invasive knee arthroplasty. The cutting systems and devices according to aspects and embodiments of the present invention are generally smaller than conventional cutting systems and devices, although their size can be adjusted to the needs of a particular surgical procedure. For installation, the systems and devices can be separated into modules. The adjustment structures and mechanisms are advantageously smaller in size and, in certain embodiments, integrate multiple adjustment capabilities, thereby reducing the total number and size of the requisite components. Employing one or more of the foregoing principles minimizes the size of the needed surgical incisions, minimizes tissue damage in general, reduces surgical repairs, and shortens the recovery time.

The modular adjustable systems and devices according to aspects and embodiments of the present invention are also particularly advantageous for computer assisted surgical procedures, such as computer-assisted knee arthroplasty. The position of the cutting systems and devices can be precisely controlled before and after installation. Thus, it is possible to fine-tune their position throughout surgery using navigational feedback.

The capabilities of the cutting systems and devices that allow their use in conjunction with computer-assisted surgery systems further minimize the damage to the patient's tissues and improve the recovery as compared to the conventional systems. In one aspect, this is because the cutting systems and devices can be positioned and installed at the bone without the encumbering mechanical referencing devices. In another aspect, the cutting systems and devices are accurately adjustable in multiple degrees of freedom, thereby allowing for more precise fit and control of the position than conventional devices, thereby achieving more accurate bone cuts and better fit of the joint prosthetic components, reducing the prosthetic's failure rate and the need for subsequent revision surgeries, and improving the patient's restoration of function. The embodiments of the present invention also provide the methods for adjusting a position of a cutting block at a bone during surgery using systems and devices according to the aspects and embodiments of the present invention.

Thus, the systems and devices according to certain embodiments of the present invention are adjustable in multiple degrees of freedom, including one or more angles of rotation and one or more translations, and are modular, with one or more modules miniature enough for minimally invasive surgery. In general, the systems according to the embodiments provided herein reduce patient visit time and costs and potential of infection. They are easier to use and manufacture, minimize tissue damage, simplify surgical procedures, are robust, can withstand multiple surgeries and required sterilization treatments, are versatile, allow for faster healing with fewer complications, require less post-surgical immobiliza-

DETAILED DESCRIPTION

Figure 1:
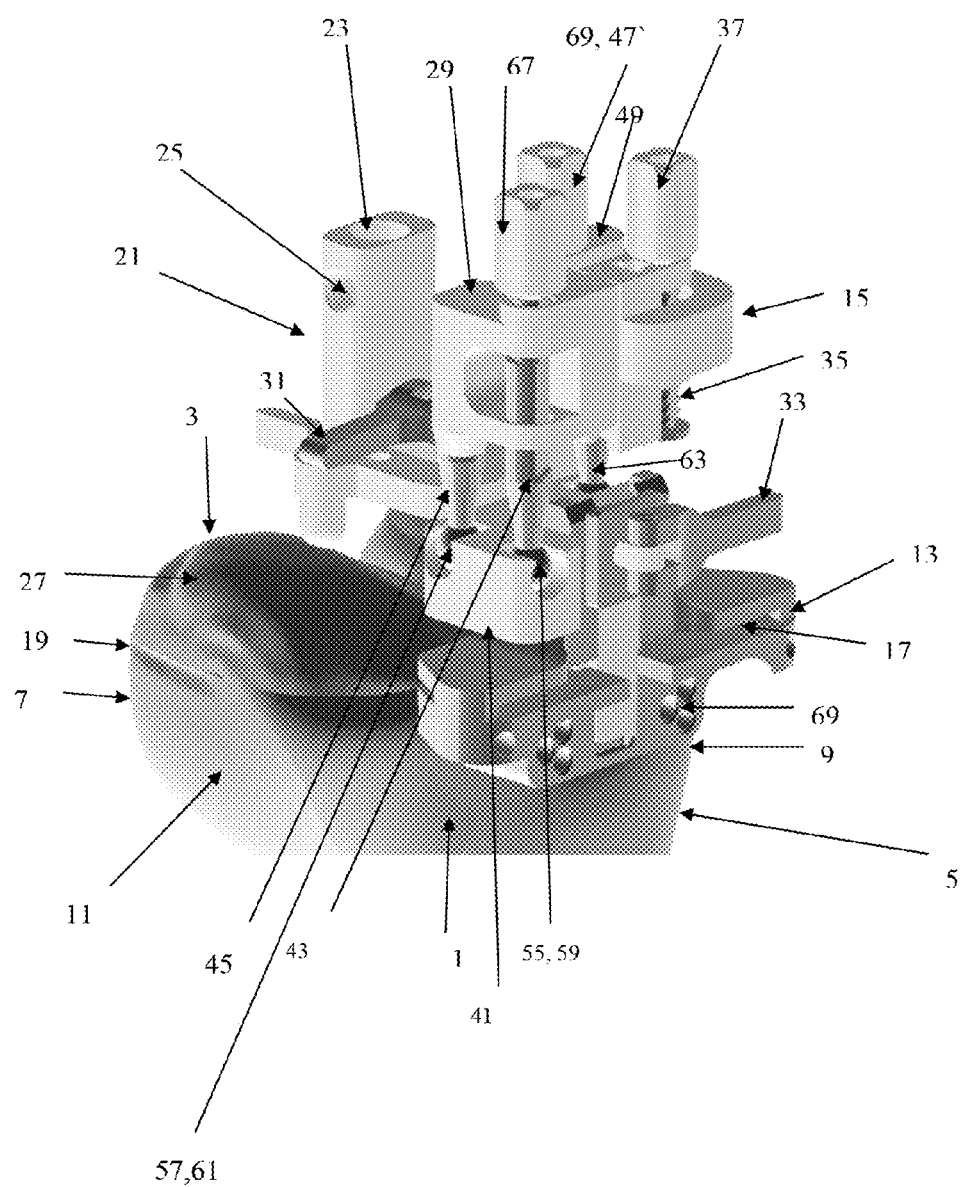
FIG. 1 is an isometric view of an adjustable cutting block attached to an end of a tubular bone.

The advantages of the systems according to the aspects and embodiments of the present invention are achieved by providing, for example, a system for preparation of a bone of a patient during total knee arthroplasty, such as the systems for resection of distal femur of proximal tibia in preparation of installation of the femoral and the tibial components, respectively, during total knee arthroplasty. However, the application principles and structures illustrated herein by the embodiments of the present invention are not limited to resection of distal femur or distal tibia and are not limited to total knee arthroplasty. Various other uses of the devices according to aspects and embodiments of the present invention are envisioned, such as, but not limited to, use in joint arthroplasty, including various knee arthroplasties, and for resection of bone tissue in any surgical procedure where precise and accurate cuts are beneficial.

The systems according to aspects and embodiments of the present invention comprise an adjustor module for adjusting the position and orientation of a cutting guide module for directing an implement for resecting the bone, for example, a surgical saw. Adjustment of the cutting guide is in least one degree of rotational freedom and at least one degree of translational freedom. In reference to the knee joint, the degrees of rotational freedoms are commonly referred to as varus/valgus angle, flexion/extension angle, and the interior/exterior axial rotation, or rotation around the long axis of a large tubular bone. The degrees of translational freedoms are commonly referred to as superior/inferior (height along the long axis of a large tubular bone), medial/lateral, and anterior/posterior. It is to be understood that the adjustment capabilities of the systems provided herein are not limited by the above terms and other notations for denoting degrees of rotational and translational freedom can be used.

The adjustor module, or the adjustor, comprises structures for stabilizing its position with respect to the patient. Such structures include, but are not limited to, structures for connecting the adjustor to the bone, such as openings for inserting attachment pins or screws, spikes, or the like. Attaching or affixing the adjustor to the patient can be performed in a variety of ways, including percutaneous attachment, direct attachment to the bone, or by engaging a structure or a surgical device fixed relative to the patient, such as, but not limited to, an anchor post or a intramedullary rod inserted into a bone. In general, stabilization of a device with respect to the patient is not limited to attaching or affixing the device to the patient, but can be accomplished by minimizing their relative movement with respect to each other using any appropriate principle or mechanism. For example, a device and a patient can be stabilized separately with respect to the surgical table. For certain applications of the present invention it is advantageous for the adjustable guide to remain as stable as possible, or have little backlash, or "play." To this end, multiple stabilization structures can be provided to be employed at the discretion of a user. One example is a combination of attachment to an anchor post with the stabilization by the additional pinning structures. In one variation, the anchor post is removed after pinning of the adjustor to the patient.

The adjustor further comprises the structures for releasably engaging one or more cutting guides, also referred to as cutting blocks, jigs, or by any other term used in the field. The cutting guide comprises one or more structures, such as a guiding slot or a guiding plane, for directing a cutting implement. As noted above, the devices according to the aspects and embodiments of the present invention allow for adjustments of the position of the cutting guide in at least one degree of rotational freedom and at least one degree of translational freedom with respect to the patient's bone. The aspects and embodiments of the present invention provide multiple adjustment capabilities to the surgical cutting guides without increasing their size or number of components. The cutting guide according to certain aspects and embodiments of the present invention further comprises structures and devices for attaching the guide to a bone, such as the distal femur or proximal tibia, prior to resection. In certain aspects and embodiments, the structures and devices provided herein comprise several parts moveable relative to one another, thereby allowing for change of position of the parts with respect to each other and the bone. The change of position can be translational or rotational or both. The moving parts are connected by one or more structures, including but not limited to, interlocking parts, rail/slot structures, t-slots, clamps, screws, pins, racks, or ball-and-socket joints.

The systems and devices of the embodiments of the present invention also comprise structures for manipulating the relative position of the parts, such as knobs, screws, levers, or the like. The systems and devices of the disclosed embodiments of the present invention can be adapted as needed for manipulation and adjustment by a user, such as a surgeon, with or without the input of a computer functionality, an automatic, robotic, or computer-aided navigating or manipulating device, or any combination or variation of the foregoing.

In a disclosed embodiment of the present invention, the user employs the systems and devices to adjust the orientation or the position, or both, of a cutting guide during knee surgery, such as TKA. Accordingly, the cutting guide is a femoral cutting guide for distal femoral resection or a tibial cutting guide for proximal tibial resection. The cutting guide can be for guiding a saw in one or more cuts. For example, the femoral cutting guide is a guide for performing one or more femoral cuts, including, but not limited to, the cuts of the distal femur, such as, distal, axially directed anterior, axially directed posterior, anterior chamfer, or posterior chamfer cuts, or a combination thereof. Integrating several guiding capabilities in the same guide, or providing the capability to engage several cutting guides to an adjustor, simultaneously or sequentially, advantageously reduces the number of components required for complete preparation of the bone. This reduction, in turn, minimizes the complexity and the size of the cutting system, rendering it particularly suitable for, although not limited to, minimally invasive surgical applications.

The cutting guide adjustor according to the aspects and embodiments of the present invention comprises one or more structures for adjusting the positon of the cutting guide at a patient's bone, such as a tibial or a femoral bone, in at least one of superior/inferior, medial/lateral, or anterior/posterior translations. The cutting guide adjustor also comprises one or more structures for adjusting the position of the cutting guide at a patient's bone, such as a tibial or a femoral bone, in at least one of varus/valgus angle, flexion/extension angle, or axial rotation. A femoral cutting guide adjustor according to one of the embodiments of the present invention comprises one or more structures for adjusting the position cutting guide with respect to the femur in at least one of varus/valgus angle, flexion/extension angle, or proximal/distal translation.

In one embodiment, the adjustor comprises a ball-and-socket structure for adjusting the cutting guide in at least two degrees of rotational freedom, comprising a plate operably connected to the cutting guide and comprising first, second, and third sockets; a first member comprising a first ball member inserted into the first socket; a second member, comprising a second ball member inserted into the second socket, a first opening, and a second opening, wherein the first member is inserted into and is retractable through the first opening in the second member; a third member; and a fourth member comprising a third ball member inserted into the third socket and a third opening, wherein the third member is inserted into and is retractable through the second opening in the second member and the third opening in the third member. Retracting or inserting at least one of the first member through the first opening or the third member through at least one of the second opening or the third opening moves the plate in at least one degree of rotational freedom, causing the cutting guide to move in the at least one degree of rotational freedom.

In one embodiment, the adjustor further comprises a module for attachment to the bone. The module for attachment to the bone can be, in turn, adjustably connected to an adjustment mechanism, such as the ball and socket structures described above. The connection between the attachment module and the adjustment mechanism is rotationally or translationally regulated, or both, thereby providing additional adjustment capabilities to the system. Providing multiple adjustment capabilities for the same or different degrees of freedom is useful in that mechanisms best suited for each adjustment step can be employed. For example, a slidable rail/slot, lever-controlled connection can be used for gross translational adjustment in a degree of freedom, whereas a screw-controlled connection can be employed to fine-tune the same adjustment. Providing mechanisms for both gross and fine adjustment control in the same system allows for more precise control of the location of the cutting block than that allowed by the conventional cutting blocks. It is also advantageous in computer-assisted surgical applications. For example, during computer-assisted surgery, the user provisionally locates the cutting block using conventional anatomical landmarks, and then fine-tunes the block's position using navigational feedback from the computer functionality.

The systems and devices according to aspects and embodiments of the present invention can include computer functionalities, imaging or navigation functionalities, or other aspects and components or systems for computer-aided surgery, or be integrated or interfaced with such systems. The systems and devices according to aspects and embodiments of the present invention can include aspects and components or systems for minimally invasive surgery, or be integrated or interfaced with such systems.

The method for adjusting a position of a cutting block at a bone during surgery using systems and devices according to the aspects and embodiments of the present invention generally comprises the following steps, not necessarily in the listed order: stabilizing an adjustor device with respect to a patient; engaging the cutting guide with the adjustor device; manipulating the adjustor to adjust the position of the cutting guide in at least one degree of translational freedom and the at least one degree of rotational freedom; attaching the cutting guide to the bone; and cutting the bone with an implement directed by the cutting guide. The method according to certain aspects and embodiments of the present invention can further comprise the step of disengaging the adjustor device from the cutting guide.

The foregoing discloses preferred embodiments of the present invention, and numerous modifications or alterations may be made without departing from the spirit and the scope of the invention.

Adjustable Cutting Block

One of the aspects and embodiments of the present invention provides an adjustable femoral cutting system, referred herein as an adjustable femoral cutting block, for performing a distal femoral cut during TKR. The adjustable cutting block is illustrated in FIGS. 1-5. The adjustable cutting block according to this embodiment is adjustable in one or more degrees of freedom. It is adjustable rotationally, translationally, or both. The principles and structures of the adjustable femoral cutting block illustrated herein can be applied to cutting blocks for resection of a variety of bones, including, but not limited to, any bone resections performed during joint arthroplasties.

The adjustable cutting block comprises mechanisms for both gross and fine adjustment of the superior/inferior translation, thereby allowing for gross and fine control of the superior/inferior position of a distal femoral cutting guide at the distal femur. The superior/inferior translation is generally along the long axis of the femur, also referred to as a distal resection depth, or height of the distal cut. Additionally, the cutting block comprises adjustment mechanisms for adjustment of the anterior/posterior translation. Providing mechanisms for both gross and fine control of the superior/anterior translation and the anterior/posterior translational adjustment allows for more precise control of the location of the distal femoral cut than that of conventional cutting blocks.

The adjustable cutting block is particularly advantageous for computer-assisted surgery. For example, during computer-assisted surgery, the user provisionally locates the cutting block using conventional anatomical landmarks and then fine tunes the block's position using navigational feedback from the computer functionality.

The adjustable cutting block is also advantageous over the conventional systems in correcting major deformities in the bony structures. The conventional instruments that rely on mechanical references to set the fixed positions for the cutting guide may reference the deformed bony geometry, making it difficult to correctly perform the cuts needed to correct the deformity. The adjustable cutting block it is not subject to this difficulty because the user does not rely on mechanical references to the bony anatomy to tune the position of the block.

Rotationally, the cutting block is adjustable in varus/valgus and flexion/extension angles. According to certain embodiments of the present invention, the rotational adjustment of the cutting block is advantageously and accurately controlled by a ball-and-socket mechanism. Integrating both varus/valgus and flexion/extension angular adjustment capabilities in the ball-and-socket structure reduces the number of components as compared to conventional adjustable cutting blocks and, in one aspect, allows for reduction in size, rendering the block particularly advantageous for minimally invasive surgical applications. The design of the ball joints employed in the preferred embodiments of the adjustable cutting block has decreased sensitivity to the manufacturing variations, providing important advantages in precision and ease of production over the conventional structures. More specifically, the screw threads adjusting the ball joints act in one axis, the only controls which affect the adjustment relate to the screw threads and the ball and socket joints themselves.

The adjustable cutting block comprises the structures for stabilizing the block at the bone, specifically, at the distal femur. For installation, the adjustable cutting block may be referenced to various virtual surgical constructs, such as a mechanical axis of the femur. Prior to adjustments, the adjustable cutting block is attached to or fixated at a bone directly or by connecting it to a surgical structure, such as, but not limited to, an intramedullary rod, a post, or an adaptor. Attaching the block to the bone or to the surgical structure does not interfere with the block's adjustment capabilities, unless so desired by the surgeon. In certain embodiments, the block's location at to the surgical structure can also be adjusted at the surgeon's discretion. In another aspect, after the adjustments of the block are completed, the cutting guide component of the block is fixated to the bone for performing the resection.

In general, during TKA the surgeon stabilizes the adjustable cutting block in the surgical field, adjusts the block's position, fixates the block in the adjusted position at the femur, and performs the distal femoral cut. In a preferred embodiment, the block comprises an adjustor component, or module, and a cutting guide component, or module. After preliminarily attaching the adjustable cutting block to the distal femur, the surgeon uses the adjustor to locate the cutting guide's position at the distal femur, fixates the cutting guide at the bone, removes the adjustor, and performs the resection.

Figure 2:
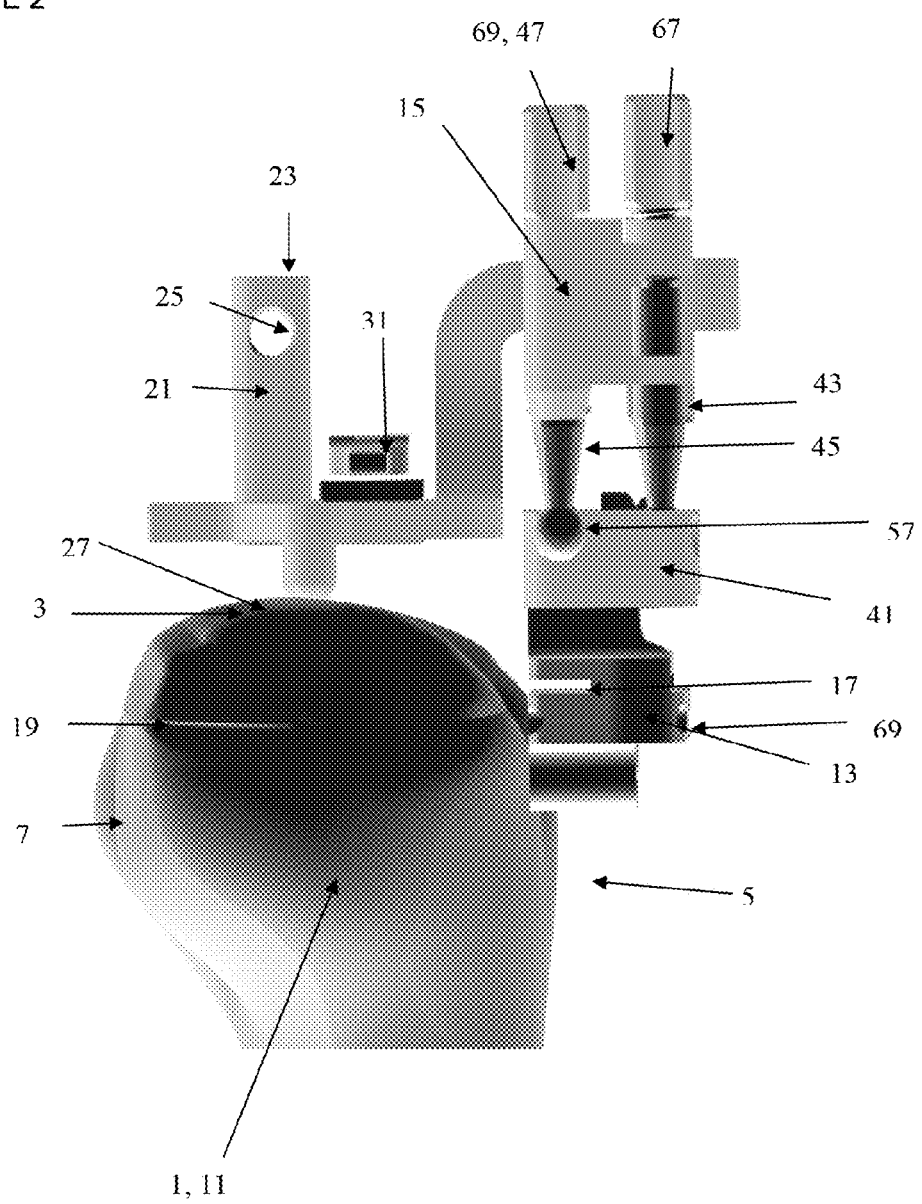
FIG. 2 is a side view in the medial/lateral direction of the adjustable cutting block of FIG. 1 attached to an end of a tubular bone.
Figure 3:
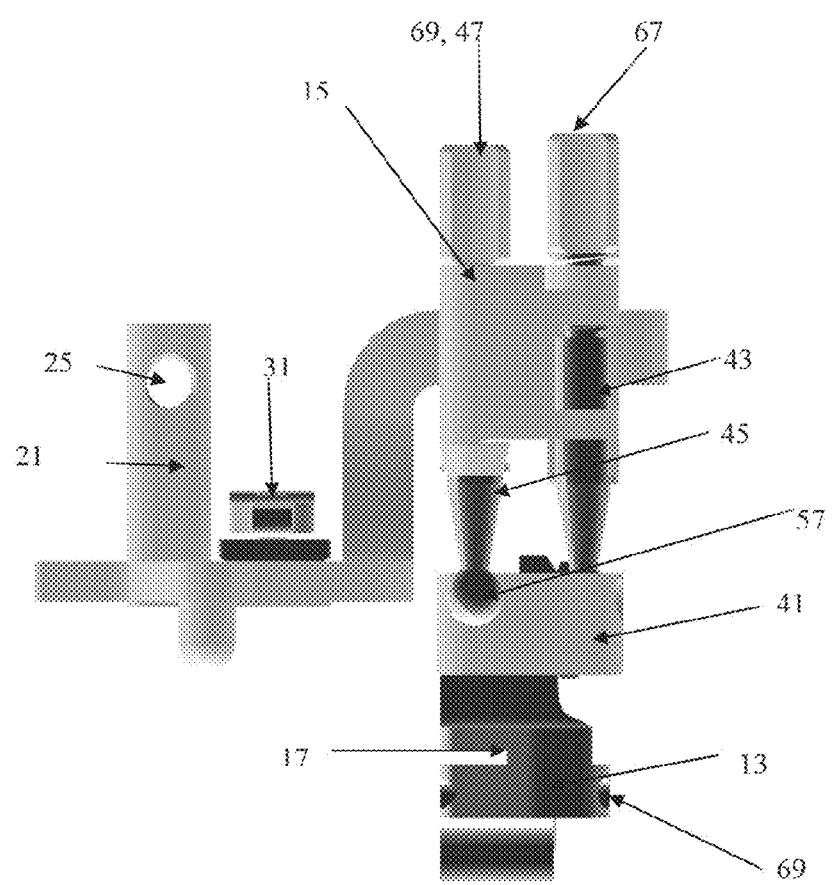
FIG. 3 is a side view in the medial/lateral direction of the adjustable cutting block of FIG. 1.
Figure 4:
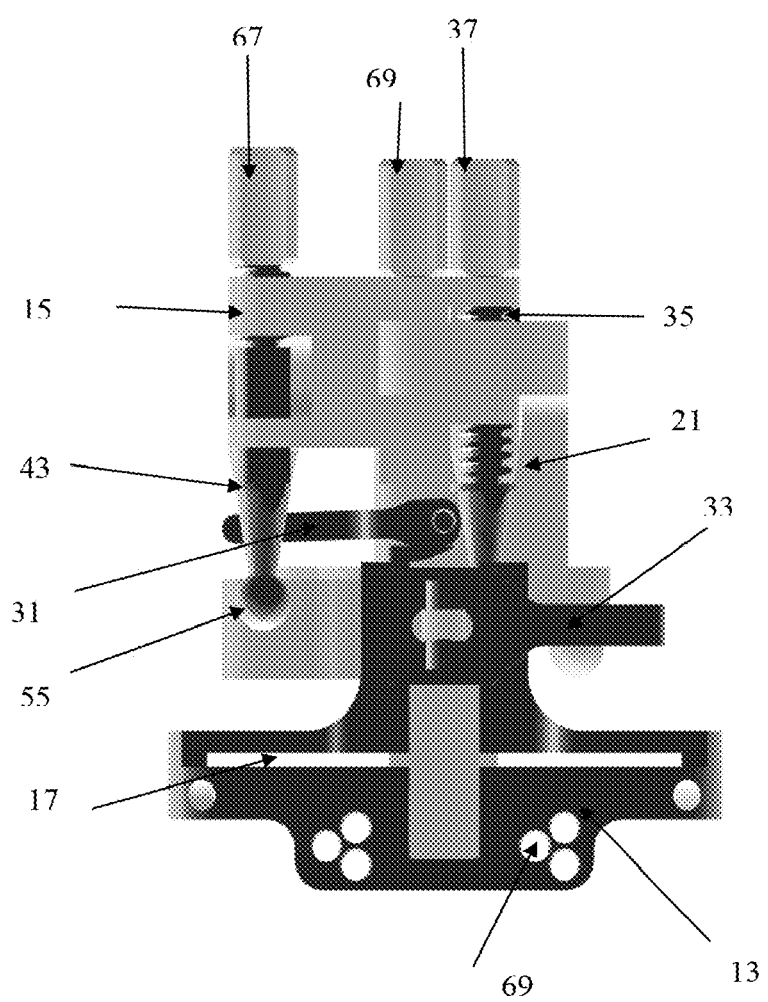
FIG. 4 is a front view in the anterior/posterior direction of the adjustable cutting block of FIG. 1.
Figure 5:
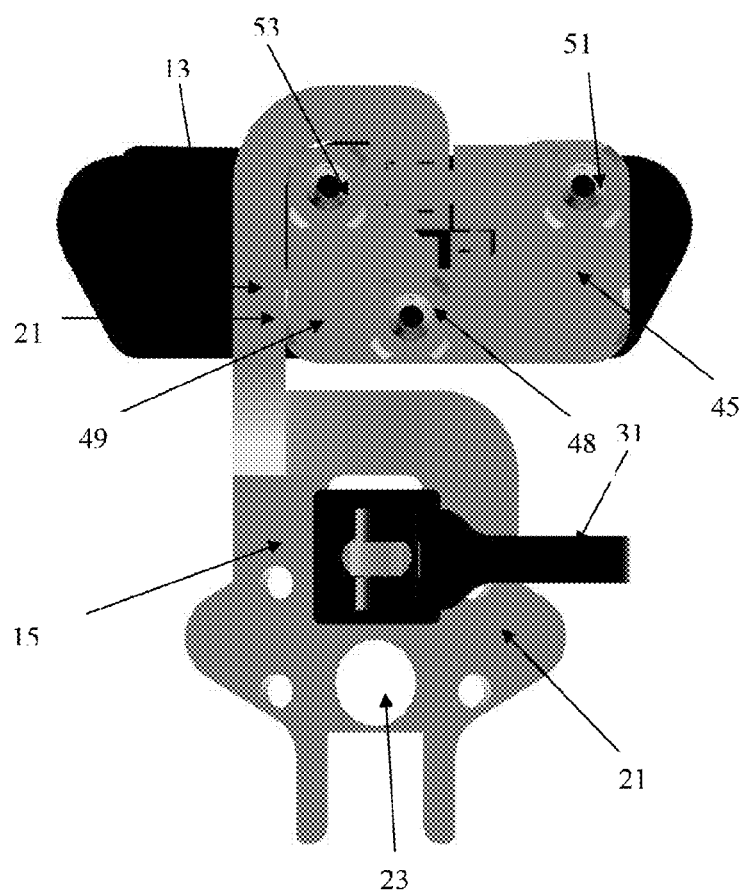
FIG. 5 is a top view in the superior/inferior direction of the adjustable cutting block of FIG. 1.
Figure 6:
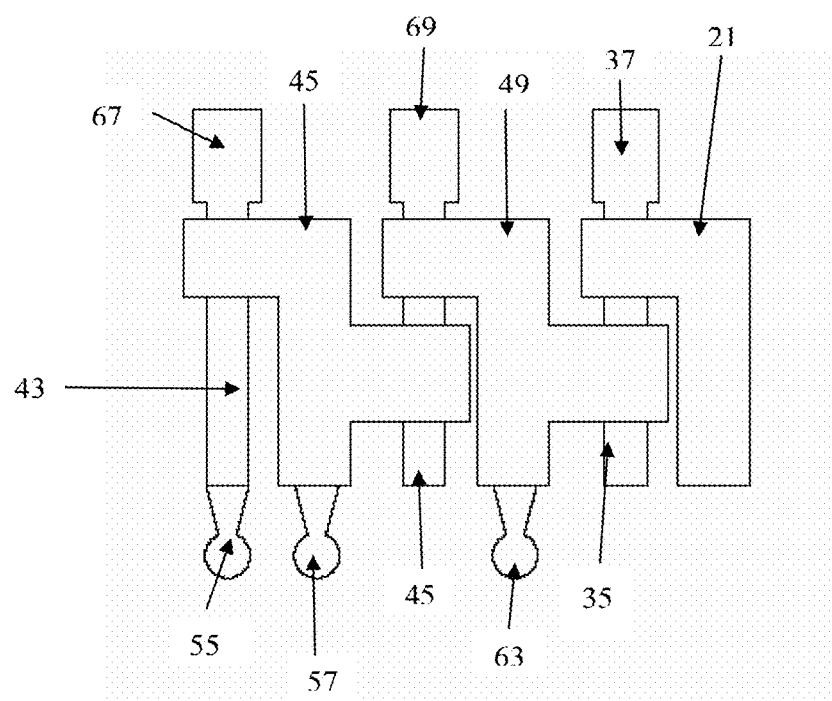
FIG. 6 is a schematic representation of the ball-and-socket structures of the adjustable cutting block.

FIGS. 1-2 show an embodiment of an adjustable cutting block positioned at a distal femur (1), whereas FIGS. 3-5 show, respectively, side, front, and top view of the adjustable cutting block. FIG. 6 schematically depicts a ball-and-socket structure of the adjustable cutting block.

The distal femur comprises distal (3), anterior (5), posterior (7), medial (9), and lateral (11) sides. The block/generally comprises a cutting guide component (13) and an adjustor component (15). Upon installation of the cutting block, the cutting guide (13) is positioned at the anterior surface (5) of the distal femur (1) and comprises, in the lengthwise medial-lateral orientation, a guiding slot (17) for guiding a surgical saw in a distal femoral cut (19) generally directed transversely to the long femoral axis. The adjustor also comprises a module (21) for attachment of the block to a femoral anchor post or an intramedullary (IM) rod. As shown in FIG. 1, the attachment module (21) comprises an opening (23) for the femoral anchor post or the IM rod. During TKA, the surgeon slides the opening (23) over the post inserted into the distal femur. After grossly adjusting the superior/inferior position of the adjustable block on the femoral post, the surgeon fixates the block on the post, for example, by a screw inserted into a corresponding threaded opening (25) directed perpendicularly to the femoral post opening. Alternatively, the block can be attached to an IM rod inserted into a femoral canal. As shown in FIG. 1, after installation, the attachment module rests on the femoral condyles (27), but it can be positioned in any desired spot at the discretion of the user.

The adjustor also comprises a ball-and-socket structure (29) connecting the attachment module (21) and the cutting guide (13). The ball-and-socket structure (29) allows angular varus/valgus and flexion/extension adjustments of the cutting guide relative to the adjustor (15) and the distal femur (1). The ball-and-socket structure (29) is adjustably attached to the attachment module (21) and to the cutting guide (13). The adjustable connections between the cutting guide (13), the ball-and-socket structure (29), and the attachment module (21) allow for the superior/inferior and the anterior/posterior translational adjustments of the cutting guide (13) at the distal femur (1).

More specifically, the ball-and-socket structure (29) is slidably connected to the attachment module (21), thereby permitting the movement of the cutting block in the anterior/posterior direction of the distal femur. This slidable connection, for example, allows sizing the anterior/posterior measurement of the adjustable cutting block to the differently sized femoral condyles. The slidable connection responsible for the block's anterior/posterior adjustment is controlled by a lever-tightening mechanism. After releasing the anterior/posterior adjustment lever (31), the user generally moves the cutting guide (13) with the ball-and-socket structure (29) in the anterior/posterior direction. After reaching the desired location, the user tightens the lever (31), thereby fixating the anterior/posterior position of the cutting guide (13) on the distal femur.

The superior/inferior position of the cutting guide (13) on the distal femur is controlled by one or more mechanisms. In the embodiment illustrated in FIGS. 1-5, the superior/inferior position is controlled by at least two mechanisms. The first mechanism is responsible for the gross superior/inferior adjustment, and the second mechanism is responsible for the fine superior/inferior adjustment. The first mechanism is a slidable connection between the ball-and-socket structure (29) and the cutting guide (13). In the embodiment illustrated in FIG. 1, the superior/inferior slidable connection between the ball-and-socket structure (29) and the cutting guide is lever-controlled (33). Releasing the lever (33) frees the slidable connection and allows the user to grossly adjust the superior/inferior position of the cutting guide (13) by moving the cutting guide relative to the ball-and-socket structure (29). After sliding the cutting guide (13) to a desired superior/inferior position, the surgeon tightens the lever (33), thereby fixating the gross superior/inferior position of the guide at the distal femur.

The second mechanism is an adjustable screw-controlled connection, or a linear way, between the ball-and-socket structure (29) and the attachment module (21) of the adjustor (15) that converts the rotation of the screw (35) into the superior/inferior translation. The user turns a knob (37) to turn the control screw (35). This moves the ball-and-socket structure (29) with the cutting guide (13) attached to it in the superior/inferior direction relative to the attachment module (21). Employing an adjustable screw-controlled connection allows the user to finely adjust the distal resection depth. As the screw (35) is turned, the ball-and-socket structure (29) moves in the superior/inferior direction (or, as a variation, in the distal/proximal direction), which, in turn, moves the attached cutting guide (13) in a like manner.

According to the preferred embodiment shown in FIGS. 1-6, the ball-and-socket mechanism allows for angular adjustments of the cutting guide's position in flexion/extension and varus/valgus. The ball-and-socket structure (29) comprises a plate (41), and four members (43, 45, 47, 49). The plate (41) is operably connected to the cutting guide (13). The first member (43) is essentially a plunger retractable through the corresponding opening (51) in the second member (45). The first member (43) and the second member (45) are respectively equipped with a first ball member (55) and a second ball member (57) placed in the corresponding sockets (59, 61) in the plate (41), thereby respectively forming a first and a second ball-and-socket joints. The third member (47) is essentially a plunger retractable through the corresponding openings (44, 48) in the second member (45) and the fourth member (49) and adjustably connecting the second member (45) and the fourth member (49). The fourth member is equipped with a ball (63) inserted into a socket (65), thereby forming a third ball and socket joint (63, 65). The sockets are shaped so that the first ball-and-socket joint (55, 59) is capable of rotating around the varus/valgus axis, and the second (57, 61) and the third (63, 65) ball-and-socket joints are capable of rotating around the flexion/extension axis.

In a preferred embodiment, the two retractable plungers (43, 47) are screws inserted into the threaded openings (51, 44, 48) and equipped with the knob controls (67, 69). Turning the first knob (67). extends or retracts the first plunger (43), translating the first ball-and-socket joint (55, 59). The extension or retraction of the first plunger (43) combined with the translationally stabilization of the second and the third ball-and-socket joints (57, 61, 63, 65) by the third member (47), causes the flexion/extension angular movement of the balls (57, 63) in the sockets (61, 65), which tilts the plate (41) in flexion/extension, and rotates the cutting guide (13) in flexion/extension.

Turning the adjustment knob (69) of the third member, also referred to as a second plunger (47), extends or retracts the plunger through the openings in the second and the fourth members (45, 47), translating the second and the third ball-and-socket joints (57, 61, 63, 65). The extension or retraction of the plunger (47) combined with the translational stabilization at the first member (43), induces rotation of the first ball (55) in its socket (59) in varus/valgus, thereby tilting the plate (41) and the cutting block (13) in varus/valgus.

As noted above, the ball-and-socket structure (29) is operably connected at its fourth member (49) to the attachment module (21) of the adjustor (15) by the superior/inferior translationally adjustable screw connection.

After completing the superior/inferior, anterior/posterior, varus/valgus, and flexion/extension adjustments, in any combination or order, the user affixes the cutting guide to the bone. As shown in FIGS. 1-5, the cutting guide comprises openings (69) for inserting screws, pins, or other fixation structures. After fixating the guide (13) to the bone, the user releases one or more connections of the cutting block to the adjustor (15) and removes the adjustor from the surgical field. The user then uses the slot (17) in the cutting guide to direct the saw blade in the distal femoral cut (19). After completing the distal femoral cut, the surgeon removes the cutting guide (13).

During TKA, the surgeons often perform the distal femoral cut first when preparing the distal femur for installation of the femoral prosthetic component. Other femoral cuts follow the distal femoral cut, with the surgeon often using the distal cut's plane as a reference to establish the position of the other resection planes. In a variation on the present embodiment, adjustable cutting blocks are provided for various femoral cuts performed during TKA. For example, the adjustable cutting blocks can be provided for cuts such as, but not limited to, a transversely directed distal femoral cut, an axially directed anterior femoral cut, an axially directed posterior femoral cut, anterior and posterior chamfer femoral cuts, a trochlear recess cut, or any combination or variation of those. The cutting blocks can be combination cutting blocks suitable for performing multiple bone cuts.

In one embodiment, the surgeon uses one or more of the adjustable cutting blocks provided by certain aspects and embodiments of the present invention to perform all the cuts during a surgical procedure. For example, performing a conventional TKA femoral resection sequence of cuts, the surgeon uses an adjustable cutting block to perform a distal femoral cut. Then, using the distal plane as a reference, the surgeon employs adjustable cutting blocks to perform axial, anterior, and posterior cuts, and any other cuts, if required, not necessarily in the above order.

Adding additional adjustment capabilities, including but not limited to an additional rotational axis, is envisioned, and falls within the aspects and embodiments of the present invention. Additional angular control is advantageous, for example, for better adjustment of the cutting guide position in the unicondylar knee surgery applications Additional angular control would also be advantageous for surgical techniques, where one cutting guide facilitates all of the cuts necessary to place the total knee prosthesis. Also possible is reduction in adjustment capabilities as preferred for a particular application.

Adjustable Transverse Cutting Block

Figure 7:
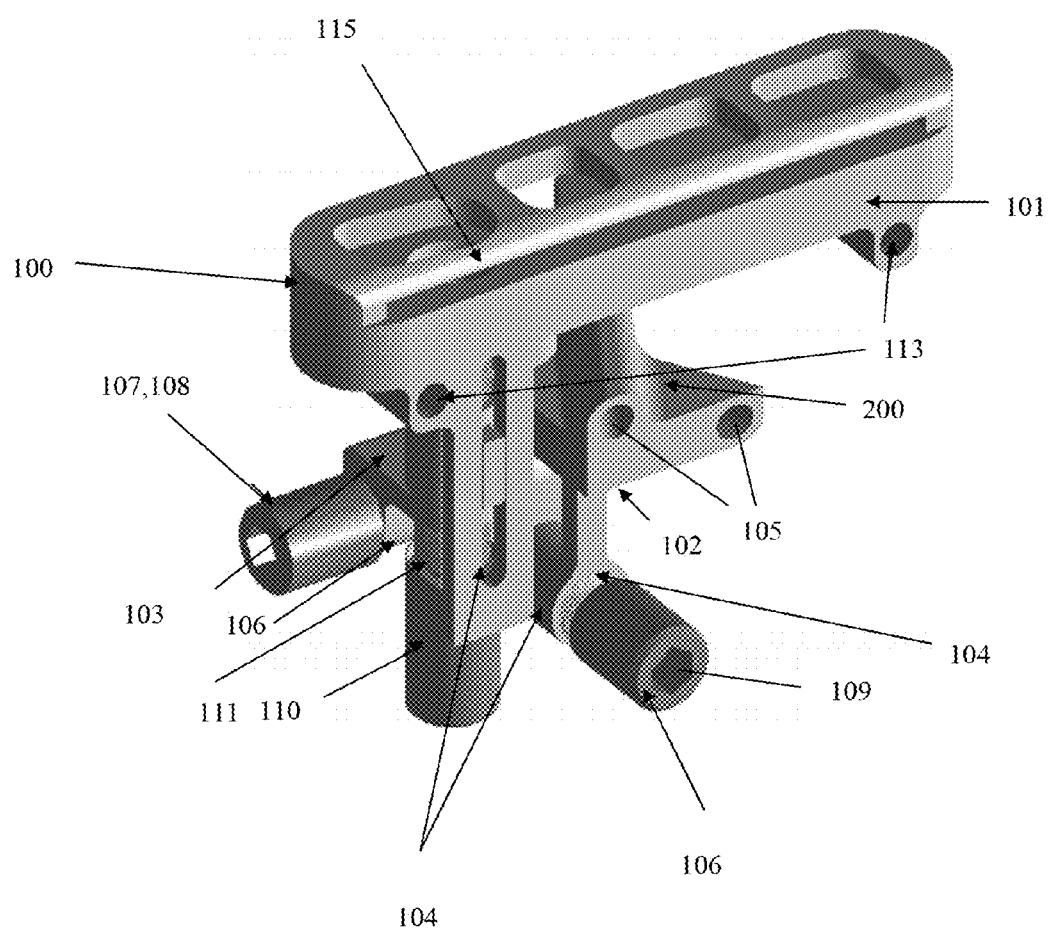
FIG. 7 an isometric view of a transverse adjustable cutting block.

In another one of its aspects and embodiments, the present invention provides an adjustable transverse cutting block (100) illustrated in FIG. 7. In a preferred embodiment, the adjustable transverse cutting block (100) is for accurately performing distal femoral cut during TKA. Adapting the block (100) for performing proximal tibial cuts during TKA is also envisioned. In general, the principles and concepts of the adjustable transverse cutting block (100) described herein can be applied to cutting blocks for performing various bone cuts during a range of surgical procedures, including, but not limited to, resection of bones during the joint arthroplasties.

The adjustable transverse cutting block (100) comprises a cutting guide (101) and an adjustor (103). In a preferred embodiment, the adjustor (103) comprises a module (102) comprising one or more structures for preliminary fixation to the bone (105), including, but not limited to, openings for screws or pins, bone spikes, pins, screws, or integrated spikes. The cutting guide (101) also comprises the structures (113) for fixation at the bone after adjustment, and a cutting slot (115) for guiding a surgical saw in a distal femoral cut.

The adjustable transverse cutting block comprises the mechanisms for angular adjustments around the varus/valgus (107) and the flexion/extension (109) axes and the mechanism for translational superior/inferior (111), or resection depth, adjustment. The adjustment mechanisms allow the user to move cutting guide (101) with respect to the adjustor (103) that has been preliminarily affixed to the bone. Thus, preliminary fixation of the cutting block does not interfere with its adjustment capabilities. In a preferred embodiment, the adjustor (103) comprises the structures for angular adjustments in flexion/extension and varusl/valgus. The device comprises a spherical joint (not shown), operably connected to the module preliminarily fixated at the bone (102) using the provided preliminary fixation structures (105). The flexion/extension adjustment knob (109) at the anterior side of the device rotates the corresponding screw (104) and tilts the module (102) in flexion/extension with respect to the varus/valgus adjustment knob (107) and the corresponding screw (106) that protrudes in the medial/lateral direction. Rotating the varus/valgus adjustment knob (107) causes rotation of the corresponding screw (104), which tilts the flexion/extension adjustment knob (109), the corresponding screw (107), and the aforementioned module (102) in the varus/valgus direction with respect to the linear way (110). The linear way (110) translates in the distal/proximal direction with the resection depth adjustment knob (111) which extends in the superior/inferior direction.

Although suitable for bone resection during any appropriate surgical application, the adjustable transverse cutting block (100) provided herein is particularly advantageous during computer-assisted surgery. The user provisionally locates the cutting block (100) using conventional anatomical landmarks, and then fine-tunes the block's position using navigational feedback. Integrating several adjustment capabilities in the same block allows reducing the number of the block's components, as well as its size as compared to the conventional adjustable cutting blocks, thereby rendering the block according to aspects and embodiments of the present invention particularly suitable for minimally invasive surgical applications.

Adding additional adjustment capabilities, including but not limited to an additional rotational axis, is envisioned, and falls within the aspects and embodiments of the present invention. Additional angluar control is advantageous, for example, for better adjustment of the cutting guide in the unicondylar knee surgery applications. Also possible is reduction in adjustment capabilities as preferred for a particular application.

When the block (100) is used during TKR, the user grossly determines the position and orientation of the block, and preliminarily fixates the block at the patient's distal femur, for example, by inserting fixation devices into the appropriate openings in the adjustor. The user then adjusts varus/valgus and flexion/extension angles of the cutting guide using the respective adjustment mechanisms. The user rotates an appropriate knob, thereby adjusting a varus/valgus or flexion/extension angle of the cutting guide relative to the femur. In a preferred embodiment, the operator first determines and adjusts the varus/valgus and flexion/extension, followed by the superior/inferior, or resection depth adjustment. This order of operation, although non-limiting, can be chosen because adjusting the angular position of the cutting guide also involves translation along the long axis of the femur. Thus, the user may prefer to adjust the angular orientation of the cutting block in flexion/extension and varus/valgus, in any order, followed by the translational adjustment of the superior/inferior position, or the resection depth.

After the desired position of the transverse adjustable cutting block is obtained, the user fixates the cutting guide using appropriate fixation devices to attach the cutting guide to the femur. In one embodiment, the adjustor is removed after the final fixation, but the adjustor can also be left in place. Upon final fixation, the user performs the distal femoral or proximal tibial cut by using the guiding slot in the guide to direct a surgical saw.

Adjustable Femoral Block

In another one of its aspects and embodiments, the present invention provides an adjustable femoral block (200). In the embodiment illustrated in FIG. 8, the adjustable femoral cutting block (200) is intended for performing axially directed anterior and posterior cuts and chamfer anterior and posterior cuts. In general, the principles and concepts of the adjustable femoral cutting block described herein can be applied to cutting blocks for performing various bone cuts during a range of surgical procedures, including, but not limited to, resection of bones during joint arthroplasties.

The adjustable femoral block (200) comprises an adjustor (201) and a cutting guide (203). The adjustor (201) comprises structures (205) for preliminary fixation to the distal femur, such as openings for inserting screws, pins, or the like. The adjustable femoral cutting block (200) comprises one or more mechanisms for adjusting the position of the cutting block component with respect to the adjustor component preliminarily fixated to the bone and to the distal femur. The adjustable cutting block is translationally adjustable in the anterior/posterior direction. Rotating an anterior/posterior adjustment screw (207) causes a centrally located pin (location shown in 209) to move in the anterior/posterior direction.

The adjustable cutting block (200) is angularly adjustable in the internal/external axial rotation around the long axis of the femur. Turning a internal/external rotation adjustment screw (211) causes a linear way to move a second rotational pin (213) positioned at a distance from the central pin (209). As the rotational pin (213) is moved with respect to the central pin (209), the cutting block is forced to rotate around the central pin (209).

The cutting guide comprises slots for directing a saw in axial (215) and chamfer (217) cuts and structures (219) for affixing the cutting guide to the bone.

During TKR, the user positions the adjustable femoral block (200) at the femur. In a preferred embodiment, the surgeon employs the adjustable femoral block after completing the distal femoral cut and, thus, uses the distal femoral cut plane as a reference for positioning the adjustable femoral block, although other surgical options are possible. After preliminarily fixating the block to the bone using the adjustor preliminary fixation structures, the user fine-tunes the anterior/posterior and flexion/extension position of the block using the respective adjustment mechanisms.

Once the cutting guide is oriented, the user affixes it to the femur using provided structures for the final fixation, such as, but not limited to, the openings for the fixation pins or screws. After the final fixation, the user removes the adjustor, thereby distally exposing the axial and chamfer saw guide slots for guiding the surgical saw in the resections. In a variation, an adjustor module of the block can be positioned anterior with respect to cutting guide component, rather than distally. This leaves the cutting slots in the guide exposed, thereby rendering it unnecessary to remove the adjustor prior to the resection.

Adding additional adjustments capabilities, including but not limited to an additional rotational axis, is envisioned and falls within the aspects and embodiments of the present invention. Reducing adjustment capabilities as preferred for a particular application is also possible.

Although suitable for bone resection during any appropriate surgical application, the adjustable femoral cutting block is particularly advantageous during computer-assisted surgery. The user provisionally locates the cutting block (200) using conventional anatomical landmarks and then fine-tunes the block's position using navigational feedback. Integrating several adjustment capabilities in the same block allows reducing the number of the block's components and its size as compared to conventional adjustable cutting blocks, thereby rendering the block according to aspects and embodiments of the present invention particularly suitable for minimally invasive surgical applications. The adjustable femoral cutting block (200) allows the user to fine-tune the position of the block within a minimally invasive incision. Further the cutting block (200) can be positioned without the encumbrance of mechanical referencing devices that complicate the surgery, are traumatic to the patient's tissues, and may interfere with the exact positioning of the block to the desired location.

Mechanized Cutting Block Adapter

Figure 9:
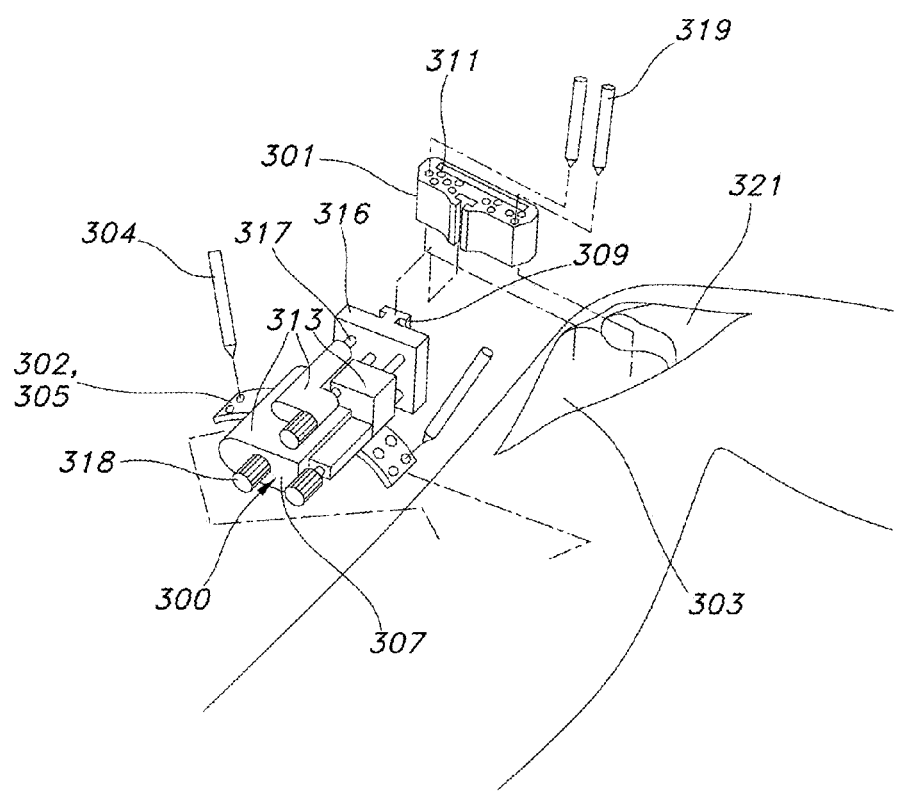
FIG. 9 is a schematic view of an adjustable cutting block adaptor at a patient's leg during surgery.

In another one of its aspects and embodiments, the present invention provides a mechanized cutting block adaptor (MCBA) illustrated in FIG. 9. The mechanized cutting block adaptor (300) is an adjustor device for positioning a cutting block during surgery. In an embodiment shown in FIG. 9, the mechanized cutting block adaptor (300) is for positioning a femoral cutting guide (301) during TKA. MCBA can also be used in resection of the proximal tibia or other bones during various joint arthroplasties. In general, using MCBA for adjusting cutting blocks during a range of surgical procedures is also envisioned. In addition to positioning cutting blocks, MCBA-like devices can be employed for locating any surgical structures or components, including, but not limited to, drill guides for adjusting the location of screws for trauma applications, such as during the distal fixation of femoral nails, positioning of the guides for performing cuts during hip replacements on the proximal femur. In general, any application where a precisely osteotomy is required, an MCBA-like device could be used to locate a guide to facilitate accurate bone resection.

Figure 8:
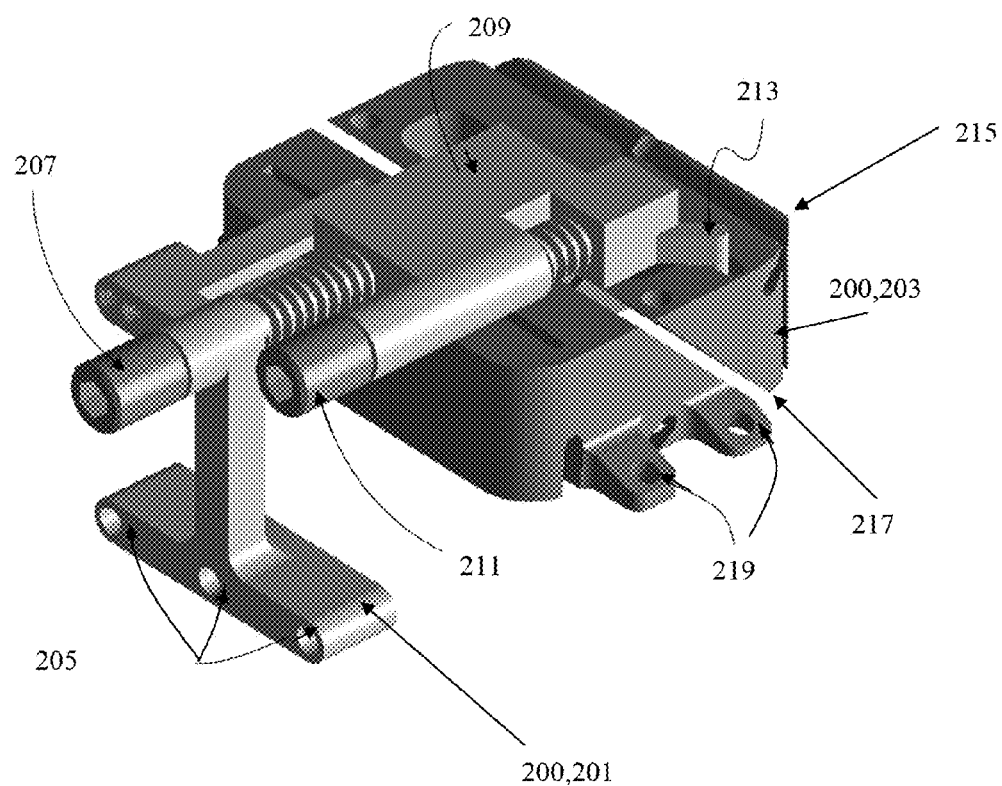
FIG. 8 is an isometric view of an adjustable femoral block.

As shown in FIG. 9, the adaptor (300) is percutaneously affixed to the patient's femur (303) using the provided openings (302) and the fixation pins (304). For operation, the adaptor (300) is operably connected to the cutting guide (301). Percutaneous installation is an example for using MCBA or similar devices, but any suitable mode of installation can be used. Installing MCBA percutaneously as shown in FIG. 8 is particularly advantageous for minimally invasive surgical applications because it minimizes the trauma to the patient's knee tissues and makes manipulating the adaptor easier. MCBA is also particularly useful for computer-aided surgical procedures, such as computer-aided TKA, because the user utilizes navigational feedback from the system to alter the position of the cutting guide using MCBA.

Among other components, MCBA comprises structures (305) for affixing the adaptor to the patient, adjustment structures or mechanisms (307), and a structure for engaging the cutting guide (301), such as the platform (309) shown in FIG. 9. In a preferred embodiment depicted in FIG. 8, the MCBA is for adjusting the position of a cutting guide (301) for performing a distal femoral cut and comprises adjustment mechanisms for translational superior/inferior, or resection depth adjustment, and varus/valgus and flexion/extension adjustments.

As shown in FIG. 9, the angular adjustment structure employs a ball-and-socket structure (307) similar to the structures described in detail elsewhere in the present application, and comprising several members (313) equipped with the balls (317) inserted into the plate (316) operably connected to the cutting guide (301), thereby forming ball-and-socket joints. The ball-and-socket structure (307) is adjustable by rotation of the screws (318) pulling or pushing one or more of its members (313), which tilts the plate (316) engaging the cutting guide (301) via the platform (309). Any other suitable adjustments structures and mechanisms can be employed, including but not limited to rack-and-pinion structures, worm gears, or spur gears.

During surgery, the user positions and affixes the MCBA to the patient in the general location and orientation of the desired cut. Before, during, or after installation, an appropriate cutting guide (301) is attached to the MCBA using the engagement structure (309). By manipulating one or more of the MCBA's adjustments mechanisms (307), the user adjusts the position of the cutting guide at the femur (303). The user can employ a computer navigation system a referencing device, such as a graduate scale, to adjust the position of the cutting block with MCBA, although any suitable referencing method can be used. In a preferred embodiment, the user adjusts superior/inferior position of the guide (301) and its flexion/extension and varus/valgus angular orientation, not necessarily in the above order. Upon adjustment, the cutting guide (301) is affixed to the patient's femur (303) within the incision using the provided fixation structures, such as openings (311) for inserting fixation pins (319). After the cutting block (301) has been affixed, the MCBA may be disengaged and removed from the cutting block (301). During TKR, the MCBA can also be used for adjustment of cutting guides at the patient's tibia (321).

Adding features to MCBA, such as, but not limited to, additional engagement components or adjustment capabilities, is envisioned and falls within the scope of the aspects and embodiments of the present invention. Such additional components and capabilities can be useful for locating surgical instruments, for example, drill guides, and can be used to adapt MCBA for various resections.

The particular embodiments of the invention have been described for clarity, but are not limiting of the present invention. Those of skill in the art can readily determine that additional embodiments and features of the invention are within the scope of the appended claims and equivalents thereto. All publications cited herein are incorporated by reference in their entirety.

What is claimed is:

1. A system for positioning a cutting guide for preparation of a bone of a patient during total knee arthroplasty, comprising: an adjustor for adjusting said cutting guide at the bone; structures operatively associated with the adjustor for adjusting the position of the cutting guide in at least one degree of rotational freedom and at least one degree of translational freedom, at least one of the structures operatively associated with the adjustor configured to convert rotational motion of the at least one structure to translational motion of the cutting guide such that rotation of the at least one structure in a first rotational direction drives the cutting guide in a first translational direction; structures for stabilizing the adjustor at the bone; and structures for engaging the cutting guide;
   wherein the adjustor further comprises a module for attaching the adjustor to the bone;
   wherein the module for attaching the adjustor to the bone is for attaching the adjustor to an anchor post or to an intramedullary rod; and
   wherein the module for attaching the adjustor to the bone is adjustably connected to ball-and-socket structures by a translationally adjustable connection.

2. The system of claim 1, further comprising the cutting guide.

3. The system of claim 2, wherein the cutting guide is a femoral cutting guide or a tibial cutting guide.

4. The system of claim 1, further comprising a femoral cutting guide for performing one or more of distal, axially directed anterior, axially directed posterior, anterior chamfer, or posterior chamfer cuts, or a combination thereof.

5. The system of claim 4, wherein the adjustor comprises one or more structures for the adjustment of the cutting guide with respect to the femur in at least one of superior/inferior, medial/lateral, or anterior/posterior translations.

6. The system of claim 4, wherein the adjustor comprises one or more structures for the adjustment of the cutting guide with respect to the femur in at least one of varus/valgus angle, flexion/extension angle, or axial rotation.

7. The system of claim 4, wherein the adjustor comprises one or more structures for the adjustment of the cutting guide with respect to the femur in at least one of vargus/valgus angle, flexion/extension angle, or proximal/distal translation.

8. The system of claim 1, wherein the module for attaching the adjustor to the bone is adjustably connected to the ball and socket structures by the translationally adjustable connection controlled by a lever or a screw.

9. The system of claim 8, wherein the ball and socket structure is connected to the cutting guide by one or more translationally adjustable connections controlled by a lever or a screw.

10. The system of claim 8, wherein the translationally adjustable connection is adjustable in one or more of superior/inferior, anterior/posterior or medial/lateral translations.

11. The system of claim 1, wherein the translationally adjustable connection is adjustable in one or more of superior/inferior, anterior/posterior or medial/lateral translations.

12. The system of claim 1, wherein the module for attaching the adjustor to the bone attaches the adjustor to the bone percutaneously.

13. The system of claim 1, wherein the adjustor is of a size suitable for minimally invasive surgery.

14. The system of claim 1, further comprising one or more fiducials for computer-assisted surgery.

15. The system of claim 1, wherein rotation of the at least one structure configured to convert rotational motion in a second, different rotational direction drives the cutting guide in a second, different translational direction.

16. A system for positioning a cutting guide for preparation of a bone of a patient during total knee arthroplasty, comprising: an adjustor for adjusting said cutting guide at the bone; structures operatively associated with the adjustor for adjusting the position of the cutting guide in at least one degree of rotational freedom and at least one degree of translational freedom; structures for stabilizing the adjustor at the bone; structures for engaging the cutting guide; and a femoral cutting guide for performing one or more of distal, axially directed anterior, axially directed posterior, anterior chamfer, or posterior chamfer cuts, or a combination thereof, wherein the adjustor comprises a ball-and-socket structure for adjusting the cutting guide in at least two degrees of rotational freedom, comprising: a plate operably connected to the cutting guide and comprising a first, a second, and a third sockets; a first member comprising a first ball member inserted into the first socket; a second member, comprising a second ball member inserted into the second socket, a first opening, and a second opening, wherein the first member is inserted into and is retractable through the first opening in the second member; a third member; and a fourth member comprising a third ball member inserted into the third socket and a third opening, wherein the third member is inserted into and is retractable through the second opening in the second member and the third opening in the third member; wherein retracting or inserting at least one of the first member through the first opening or the third member through at least one of the second opening or the third opening moves the plate in at least one degree of rotational freedom, causing the cutting guide to move in the at least one degree of rotational freedom.

17. A system for positioning a cutting guide for preparation of a tibial or femoral bone of a patient during total knee arthroplasty, comprising: the cutting guide; an adjustor for adjusting said cutting guide at the bone; one or more structures operatively associated with the adjustor for adjusting the position of the cutting guide with respect to the bone in at least one of vargus/valgus angle, flexion/extension angle, or proximal/distal translation; a ball-and-socket structure for adjusting the position of the cutting guide in at least two degrees of rotational freedom, comprising: a plate operably connected to the cutting guide and comprising a first, a second, and a third sockets; a first member comprising a first ball member inserted into the first socket; a second member, comprising a second ball member inserted into the second socket, a first opening, and a second opening, wherein the first member is inserted into and is retractable through the first opening in the second member; a third member; and a fourth member comprising a third ball member inserted into the third socket and a third opening, wherein the third member is inserted into and is retractable through the second opening in the second member and the third opening in the third member; wherein retracting or inserting at least one of the first member through the first opening or the third member through at least one of the second opening or the third opening moves the plate in at least one degree of rotational freedom, causing the cutting guide to move in the at least one degree of rotational freedom; a module for attaching the adjustor to a anchor post or to an intramedullary rod; and structures for engaging the cutting guide.

* * * * *